(12) United States Patent
Evans et al.

(10) Patent No.: US 7,833,278 B2
(45) Date of Patent: *Nov. 16, 2010

(54) DEVICES AND METHODS FOR TREATING DEFECTS IN THE TISSUE OF A LIVING BEING

(75) Inventors: Douglas G Evans, Downingtown, PA (US); Scott M. Goldman, Paoli, PA (US); Russell T. Kronengold, Lansdale, PA (US)

(73) Assignee: Kensey Nash BVF Technology, LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/254,337

(22) Filed: Oct. 20, 2008

(65) Prior Publication Data

US 2009/0043400 A1 Feb. 12, 2009

Related U.S. Application Data

(63) Continuation of application No. 11/775,672, filed on Jul. 10, 2007, which is a continuation of application No. 10/631,431, filed on Jul. 31, 2003, now Pat. No. 7,241,316, which is a continuation of application No. 10/171,248, filed on Jun. 13, 2002, now Pat. No. 7,166,133.

(51) Int. Cl.
*A61F 2/28* (2006.01)
(52) U.S. Cl. .............. 623/23.51; 623/23.56; 623/23.58; 623/23.61
(58) Field of Classification Search ........................ None
See application file for complete search history.

(56) References Cited

U.S. PATENT DOCUMENTS

| 4,412,947 A | * | 11/1983 | Cioca ........................ 530/356 |
| 4,834,734 A | * | 5/1989 | Morganti ..................... 604/368 |
| 4,948,540 A | * | 8/1990 | Nigam ......................... 264/28 |
| 6,183,498 B1 | * | 2/2001 | Devore et al. ................ 606/214 |
| 2002/0183855 A1 | * | 12/2002 | Yamamoto et al. ....... 623/23.51 |

OTHER PUBLICATIONS

Armstrong, Robert B. et al., "Punch biopsy wounds treated with Monsel's solution or a collagen matrix," Arch. Dermatol., May 1986, 122:546-549.
Kubler, Norbert et al., "Bone morphogenetic protein-mediated interaction of periosteum and diaphysis," Clinical Orthopaedics and Related Research, Sep. 1990, 258:279-294.
Noah, Ernst Magnus et al., "Impact of sterilization on the porous design and cell behavior in collagen sponges prepared for tissue . . . " Biomaterials, 2002, 23:2855-2861.
Stone, Kevin R. et al., "Porcine and bovine cartilage transplants in cynomolgus monkey," Transplantation, Mar. 1997, 63: 640-645.
Truumees, Eeric et al., "Alternatives to autologous bone harvest in spine surgery," U of Penn. Orthopaedic J., 1999, 12:77-88.
Zetkin, Maxim et al., "Lexikon der Medizin," 1999, 1068, "Kollagen.".

* cited by examiner

*Primary Examiner*—David H Willse
*Assistant Examiner*—Javier G Blanco
(74) *Attorney, Agent, or Firm*—Jeffrey R. Ramberg

(57) ABSTRACT

An implant for deployment in select locations or select tissue for regeneration of tissue is disclosed. The implant includes collagen and or other bio-resorbable materials, where the implant may also be used for therapy delivery.

24 Claims, 16 Drawing Sheets

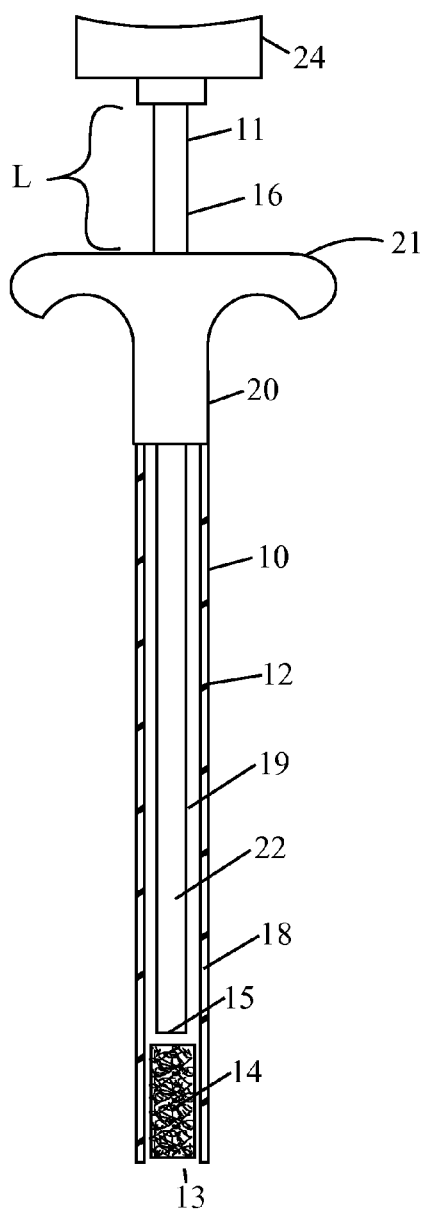
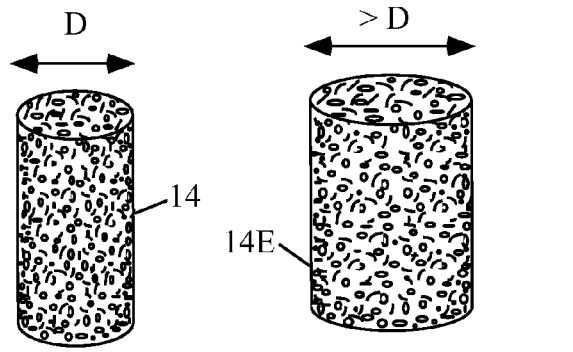
FIG. 2A  FIG. 2B
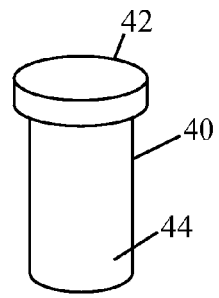
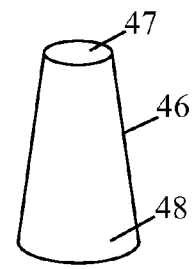
FIG. 2C  FIG. 2D
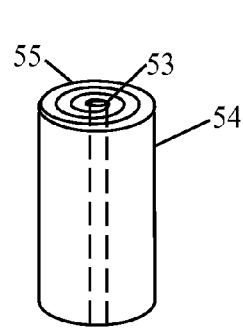
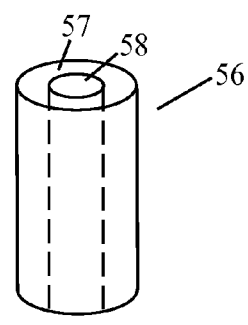
FIG. 1  FIG. 2E  FIG. 2F

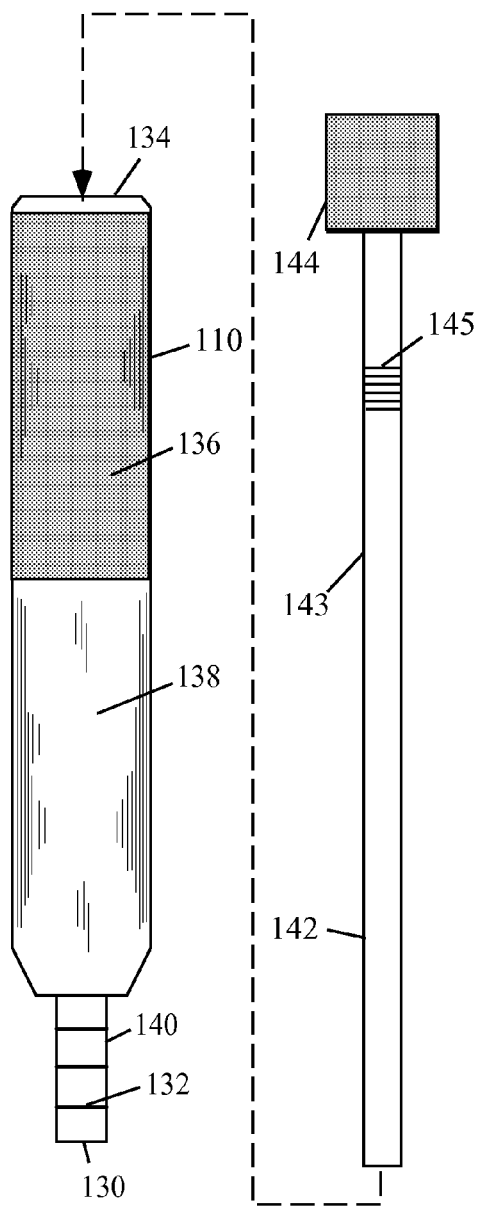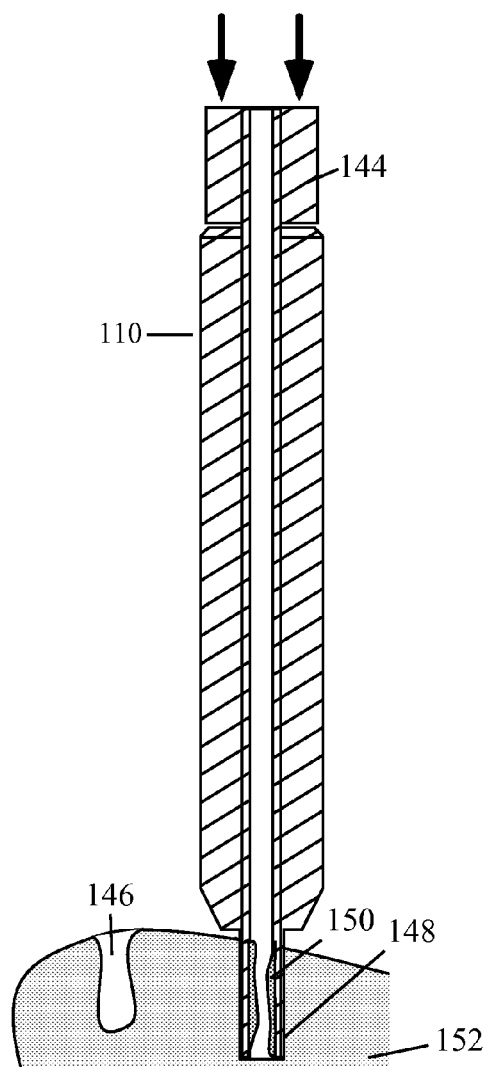
FIG. 10
FIG. 11

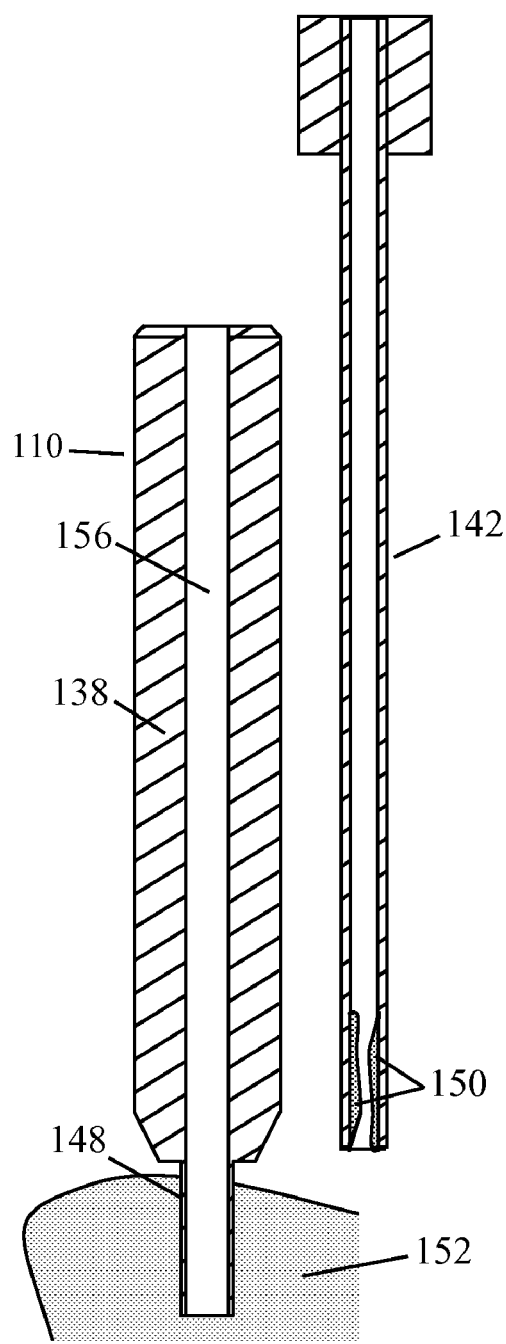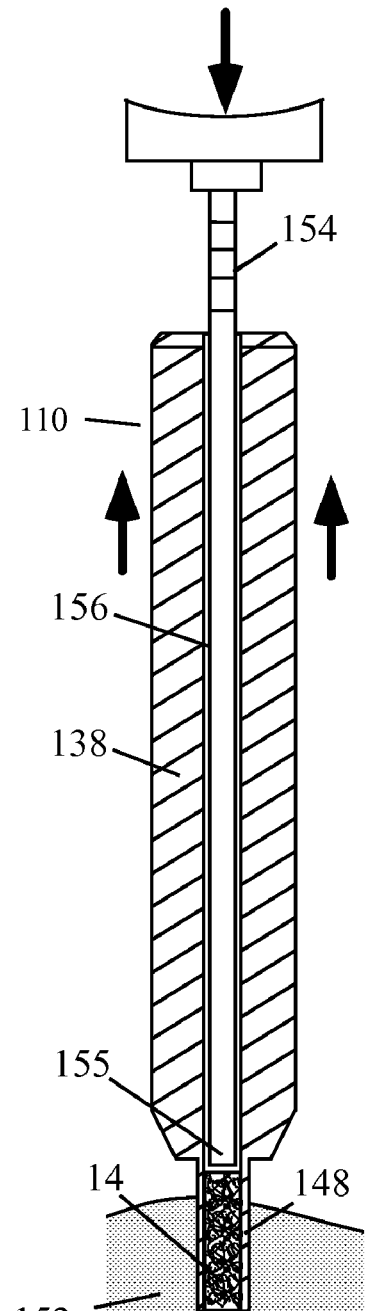
FIG. 12  FIG. 13

DEVICES AND METHODS FOR TREATING DEFECTS IN THE TISSUE OF A LIVING BEING

CROSS REFERENCE TO RELATED APPLICATIONS

This application is a continuation of U.S. patent application Ser. No. 11/775,672, filed Jul. 10, 2007, which is a continuation of U.S. patent application Ser. No. 10/631,431, filed Jul. 31, 2003, now U.S. Pat. No. 7,241,316, which is a continuation of U.S. patent application Ser. No. 10/171,248, filed Jun. 13, 2002, now U.S. Pat. No. 7,166,133, which are assigned to the same assignee as this invention and whose disclosures are fully incorporated by reference herein.

BACKGROUND OF THE INVENTION

This invention relates generally to medical devices and procedures and more particularly to devices and methods for treating defects in the tissue of a living being.

To better treat our aging population, physicians are looking for new and better products and methods to enhance the body's own mechanism to produce rapid healing of musculoskeletal injuries and degenerative diseases. Treatment of these defects has traditionally relied upon the natural ability of these types of tissue to repair themselves. In many instances the body is unable to repair such defects in a reasonable time, if at all. Advances in biomaterials has allowed for the creation of devices to facilitate wound healing in both bone and soft tissues defects and injuries. Such devices are used in tissue regeneration as tissue (e.g. bone) graft scaffolds, for use in trauma and spinal applications, and for the delivery of drugs and growth factors.

Bone and soft tissue repair is necessary to treat a variety of medical (e.g. orthopedic) conditions. For example, when hard tissue such as bone is damaged as a result of disease or injury, it is often necessary to provide an implant or graft to augment the damaged bone during the healing process to prevent further damage and stimulate repair. Such implants may take many forms (e.g. plugs, putties, rods, dowels, wedges, screws, plates, etc.) which are placed into the tissue. Typically, such implants can be rigid, flexible, deformable, or flowable and can be prepared in a variety of shapes and sizes. For rigid implants (e.g. bone screws), the defect site is typically preconditioned by forming a depression, channel, or other feature (e.g. pre-tapped hole) therein in preparation for the application of the implant. For non-rigid structural repair materials (e.g. putties and pastes) to be conveniently used, they must be capable of being formed into a variety of complex shapes to fit the contours of the repair site. An accurately configured implant that substantially fills the defect site will enhance the integration of natural bone and tissue to provide better healing over time. For example, when repairing defects in bone, intimate load carrying contact often is desired between the natural bone and the bone substitute material to promote bone remodeling and regeneration leading to incorporation of the graft by host bone.

Current bone graft materials include autografts (the use of bone from the patient), allografts (the use of cadaver bone), and a variety of other artificial or synthetic bone substitute materials. Autografts are typically comprised of cancellous bone and/or cortical bone. Cancellous bone grafts essentially provide minimal structural integrity. Bone strength increases as the implant incorporates surrounding cells and new bone is deposited. For cortical bone, the graft initially provides some structural strength. However, as the graft is incorporated by the host bone, nonviable bone is removed by resorption significantly reducing the strength of the graft. The use of autograft bone may result in severe patient pain and other complications at the harvest site, and there are limitations to the amount of autograft bone that can be harvested from the patient. Allografts are similar to autografts in that they are comprised of cancellous and/or cortical bone with greater quantities and sizes being typically available. Disadvantages of allografts include limited supplies of materials and the potential for transmission of disease. The disadvantages of the existing products creates a need for a better devices and methods for treating defects in the tissue of a living being.

Collagen is the most abundant protein found in the body. The unique chemistry of collagen makes it an ideal material for structural and hemostatic applications in both clinical and diagnostic settings. Collagen, like all proteins, is comprised of amino acids linked covalently through peptide or amide linkages. The sequence of the amino acids, or the primary structure, outlines the three-dimensional structure of the protein which in turn dictates the function and properties of the molecule. Collagen is composed of three peptide chains associated in a triple helical orientation. These triple helices associate to form fibrils which ultimately make up connective tissue and other structural member.

Collagen has been used in a number of applications in the art. For example, one application is for use in hemostatic devices for the stoppage of bleeding, such as is described in U.S. Pat. No. 5,310,407 (Casal) and U.S. Pat. No. 4,890,612 (Kensey). However, neither teaches the use of native insoluble fibrous collagen. In U.S. Pat. No. 5,425,769, Snyders, Jr. discloses a biocompatible and bioresorbable bone substitute with physical and chemical properties similar to bone, consisting of reconstituted fibrillar collagen within a calcium sulfate di-hydrate matrix. The ratios of calcium sulfate and collagen are adjusted for each application and the bone substitute is molded in situ to form a solid phase. Similarly, U.S. Pat. No. 5,425,770 (Piez, et. al.) discloses a composition made from a calcium phosphate particulate mineral such as hydroxyapatite or tricalcium phosphate mixed with atelopeptide reconstituted fibrillar collagen for conductive bone repair. U.S. Pat. No. 5,904,718, (Jefferies) describes a process and invention comprising demineralized bone particles and collagen. Examples of medical implants that utilize reconstituted fibrous collagen include U.S. Pat. No. 4,642,117 (Nguyen, et al.), U.S. Pat. No. 4,795,467 (Piez, et al.), and U.S. Pat. No. 5,997,896 (Carr, et al.). The '718, '769 and '770 patents, all require the use of reconstituted collagen.

U.S. Pat. Nos. 4,563,350 and 4,888,366 describe the use of lyophilized and preformed collagen carriers of osteoinductive factors in bone repair, respectively. When used as preformed solid implants, these carriers consist generally of ceramic materials which are held together by collagen. Similarly, U.S. Pat. No. 4,776,890 describes non-crosslinked collagen/mineral implants, which can be moistened and molded into a desired shape before implantation. Therein, crosslinking is described as being undesirable because of its inhibitory effects on bone in-growth. U.S. Pat. Nos. 4,795,467, 5,035,715 and 5,110,604 describe porous collagen-containing implants for use in bone repair and/or wound healing. U.S. Pat. No. 4,948,540 (Nigam) describes a type of fibrous native collagen for use as a hemostatic dressing. These references do not teach or suggest the solution to the ubiquitous problem of high porosity and excessive resilience in a collagen-containing implant material for bone defect repair.

Devices made from compressed collagen matrices include Robinson et al. (Cardiovasc Intervent Radiol 1990; 13:36-39), who described the use of compressed collagen plugs prepared from Gelfoam™ (manufactured by Pharmacia & Upjohn Company, Kalamazoo, Mich.) to repair biopsy tract defects in lungs. Armstrong et al. (Arch Dermatol 1986; 122: 546-549) described the use of compressed collagen plugs prepared from Helistat™ (manufactured by Integra Life-Sciences) to repair cutaneous biopsy wounds. All of these references teach the use of collagen but none teach the use of the multi-phasic composition of the present invention, furthermore the function of these devices is for stopping the bleeding from a puncture and not for regenerating tissue.

Accordingly, a need remains for a defect filling material, prepared primarily of collagen, which has improved mechanical stability and is adequately dense and sufficiently conformable for medical or surgical utility.

U.S. Pat. No. 6,110,484 (Sierra) describes an implant formed in situ, that contains a biodegradable porosifying agent; however the embodiment is a pre-formed solid plug and porosity is not rapidly created following implanting, to form an osteoconductive structure. Therefore, a need exists for an implant that rapidly becomes porous following implantation.

Various embodiments of these devices include polysaccharides in the construct. Polysaccharides are a key component of the extracellular matrix component of bone and related tissue, since they provide hydrophilicity and important structural aspects. When incorporated into medical implants, polysaccharides also impart hydrophilicity and help to regulate the wound healing response associated with the implant, as well as improve cell attachment. The combination of Polysaccharides and collagen has been described by U.S. Pat. No. 4,614,794 (Easton, et. al.) and U.S. Pat. No. 5,972,385 (Liu, et. al.). '794 is limited to fabrication from a hydrolytic degradation process, and the '385 device must be crosslinked. Therefore, a need exists for a polysaccharide that is not limited to fabrication from a hydrolytic degradation process, and the that does not require cross-linking.

Demineralized bone alone may be useful for repair of bony defects, there is much inconsistency because bone is a natural material. Some approaches to harvesting these minerals include defatting, grinding, and calcining or heating the bone. However, the resulting mixture of natural bone mineral is chemically and physically variable. Additionally, allogenic bone from cadavers must be harvested carefully under rigid conditions and then properly stored in tissue banks to prevent possible immunologic complications or possible transmission of viral or bacterial pathogens. Sterilization of demineralized bone may alter the physiochemical properties critical for bone induction when methods such as gamma radiation employed. It is recognized that irradiation of demineralized bone powder before implantation weakens the osteogenic response by approximately 20%. It is therefore extremely difficult to use natural bone as an implant, thus there remains a need for a synthetic bone replacement material.

In U.S. Pat. No. 5,425,769, (Snyders, Jr., et al.) teaches that there have been many attempts to enhance the handling and osteogenic ability of calcium phosphate implants by incorporation of calcium phosphate granules into a binding matrix such as plaster of Paris or soluble or reconstituted fibrous collagen. This will improve the workability of the implant and encourage bony in-growth through partial resorption of the implant. Disadvantages of this conjugate include the inability of the malleable collagen matrix to attain a solid state in vivo and the resistance of solidifying plaster matrices to molding. The is overcome by the present invention with a unique blend of soluble and native fibrous collagen which maintains its strength following implantation, while still remaining somewhat compliant, without the need for ceramic additives; although, the present invention contemplates the potential improvement of their use.

In U.S. Pat. No. 4,394,370, Jefferies describes an implant made of reconstituted collagen and either demineralized bone or else bone morphogenic protein, and which when implanted into bone, will cause osteogenesis. The collagen may be chemically cross-linked. The physical properties of these sponges is not specified in the disclosure, however, reports of the handling of similar collagen sponges indicates these materials to be very weak and quickly resorbable (no wet tear strength and resorption in 1 to 2 weeks).

Additionally, in U.S. Pat. No. 4,430,760, Smestad describes an implant consisting of demineralized bone or dentin inside of a container made from either fibers such as collagen or a microporous membrane. The pores of the implant are sized so that it selectively allows osteocytes and mesenchymal cells to pass, but does not allow the particulate demineralized bone or dentin to pass through. The problem concerning this patent is that it can not be used in load-bearing locations. Therefore, a need exists for an implant that will maintain structural or mechanical integrity following implant.

In U.S. Pat. No. 4,440,750, Glowacki et al. describe an aqueous dispersion of reconstituted collagen fibers mixed with demineralized bone particles for use in inducing bone formation. This graft material possesses little physical strength and mechanical properties and thus, its uses are limited. Furthermore, with time, the demineralized bone particle suspended within the aqueous collagen sol-gel begin to settle under gravitational forces, thus producing an non-homogeneous or stratified graft material; whereas the present invention provides strength, and does not utilize sol-gel processing thereby avoiding any settling of gel constituents, or other unintentional non-homogeneity. Additionally, U.S. Pat. No. 4,485,097 (Bell) describes a material composed of a hydrated collagen lattice, fibroblast cells, and demineralized bone powder. This material is in the form of a hydrated collagen gel, and therefore has minimal physical strength or mechanical integrity. Therefore, the material fails to meet the aforementioned shortcomings in the art.

In U.S. Pat. No. 4,623,553, Ries et. al. describes a method for producing a bone substitute material consisting of collagen and hydroxyapatite and partially crosslinked with a suitable crosslinking agent, such as glutaraldehyde or formaldehyde. The order of addition of these agents is such that the crosslinking agent is added to the aqueous collagen dispersion prior to the addition of the hydroxyapatite or calcium phosphate particulate material. The resultant dispersion is mixed and lyophilized. The '553 patent lacks any components which are known osteogenic inducers, such as demineralized bone matrix or extracted bone proteins. Similarly, U.S. Pat. Nos. 4,865,602 and 5,035,715, (Smestad, et. al.) describe a process for preparing a biocompatible bone implant composed of atelopeptide fibrillar reconstituted collagen and a mineral component which may be calcium phosphate, hydroxyapatite, or tricalcium phosphate. The implant is gamma sterilized with enough irradiation to cause crosslinking of the collagen in order to produce the desired handling and mechanical properties for the implant. The '602, '715, and '553 patents differ from the present invention in that they require crosslinking, which is suspected to be detrimental to in-growth, additionally, the '602 and '715 patents include a reconstituted collagen matrix.

In U.S. Pat. No. 5,071,436 Huc et. al. describe a new bone-substitute biomaterial which is a combination of collagen, hydroxyapatite, and glycosaminoglycans and in the form of a sponge. The concentration of the glycosaminoglycans is preferably between 1 and 2% per liter of 1% collagen gel. The concentration of the hydroxyapatite and the collagen to each other is preferably about equal, which is six times greater than the concentration of glycosaminoglycan component.

In U.S. Pat. No. 5,320,844, Liu et. al. describes a composite material for hard tissue replacement whose properties are similar to natural bone. The synthetically derived, homogenous composite contains a collagen component and a calcium phosphate-containing component precipitated from a liquid medium.

In U.S. Pat. No. 5,711,957, Patat et al. discloses an implant made of a porous calcium carbonate-based material as an external wall to support a growth factor. These authors also teach why they believe that the presence of collagen is neither necessary nor desirable in the case when the implant is intended to be used as a bone-formation implant, regardless the external wall of '957 is the only region housing a growth factor.

In U.S. Pat. No. 5,904,718, Jefferies describes a chemically cross-linked matrix of demineralized bone particles or collagen which may or may not contain a drug or mineral additive. The '718 patent discloses that the cross-linking enables the construct to have a mechanical strength. Further, the '718 patent discloses that the cross-linking can conjugate the drug or mineral to the organic matrix. Embodiments of the current invention do not rely on crosslinking for strength, nor does it rely on crosslinking for conjugation of drugs or other therapies; this is an important feature of the present invention, since crosslinking has been shown by others to inhibit tissue ingrowth.

The fabrication of and application of microspheres is known and as such the following examples are included herein as reference. U.S. Pat. No. 3,887,699 describes a solid biodegradable polymer spheroid implants which incorporate a drug for sustained release as the polymer naturally degrades in the human body. Many different methods of constructing this type of controlled release system have been developed. Although the uniform matrix of a polymer provides a simple and efficient structure for the controlled release of agents with microspheres, many advanced methods of containing and releasing the therapeutic agents have been developed. U.S. Pat. No. 4,637,905 (Gardner) discloses a method for encapsulating a therapeutic agent within a biodegradable polymer microsphere. U.S. Pat. No. 4,652,441 (Okada et al.) discloses a method of utilizing a water-in-oil emulsion to give prolonged release of a water-soluble drug. The patent describes a wide variety of drugs that can be delivered via prolonged release micro-capsules as well as suitable polymeric materials and drug retaining substances. It is conceived that the system of this invention could incorporate any of the drugs described to in this patent to generate a beneficial effect in the cardiac tissue. U.S. Pat. No. 5,718,921 (Mathiowitz et al.) discloses a method for constructing a multiple layer microsphere which can release two different drugs at controlled rates or a singe drug at two different rates. U.S. Pat. No. 5,912,017 (Mathiowitz et al.) also discloses a method of forming two layered microspheres by using an organic solvent or melting two different polymers, combining them with a desired substance and cooling. Microspheres are not limited to just water-soluble therapeutic agents. See, for example, U.S. Pat. No. 5,288,502 (McGinity et al.) which discloses a multi-phase microsphere which is capable of incorporating water-soluble and water-insoluble drugs.

SUMMARY OF THE INVENTION

This invention includes various aspects. For example there is provided a system and method for treating tissue within the body of a living being. The current invention essentially comprises a synthetic tissue substitute material and a method and system for deploying the implant. Some of the significant advantages and features of the various embodiments of the present invention include, but are not limited to, the following characteristics:

1) It is an object of the present invention to provide an implant that is generally fabricated from one or more biocompatible materials that will act as a scaffold for the in-growth of tissue. Example materials include polymers (e.g. polyesters, collagen, polysaccharides), ceramics, and metals;
2) It is an object of the present invention to provide an implant that can contain a material that maintains the required level of physical integrity after implantation;
3) It is an object of the present invention to provide an implant wherein, at least a portion of, if not all of, the device when implanted will resorb after it is no longer needed;
4) It is an object of the present invention to provide an implant that serves to restore the mechanical, architectural and structural competence to the tissue defect or bone void being treated;
5) It is an object of the present invention to provide an implant that contains a depot of material (e.g. calcium salts, collagens, cytokines, drugs, etc.) for assisting the in-growth of cells;
6) It is an object of the present invention to provide an implant that may provide a biologically acceptable and mechanically stable surface structure suitable for genesis, growth and development of new connective tissue (e.g., non-calcified, calcified);
7) It is an object of the present invention to provide an implant that can act as a carrier for the other constituents of the invention which do not have mechanical and structural competence (e.g. soluble collagen, drugs, biologics, cells, etc.);
8) It is an object of the present invention to provide an implant that can act as a carrier for the other constituents of the invention which act to beneficially treat the living being in which they are implanted (e.g. drugs, biologics, cells, radioisotopes, platelet rich plasma, etc.);
9) It is an object of the present invention to provide an implant that can, when used for bone applications, and certain other applications as are described herein, the implant provides an osteoconductive matrix providing a scaffold for bone in-growth.
10) It is an object of the present invention to provide an implant that can incorporate osteoinductive factors providing chemical agents that induce bone regeneration and repair.
11) It is an object of the present invention to provide an implant that can incorporate osteogenic cells for providing the basic building blocks for bone regeneration by their ability to differentiate into osteoblasts and osteoclasts.
12) It is an object of the present invention to provide an implant that can also provide structural integrity to the defect and surrounding tissues to a level that is suitable for some load to be carried by the implant.
13) It is an object of the present invention to provide an implant that can provide a biocompatible alternative for utilizing autologous bone (e.g. from the illiac crest or rib) or other tissue for grafting purposes;

14) It is an object of the present invention to provide an implant that can create an environment which is conducive to tissue regeneration (e.g. osteogenesis) in its own right;

15) It is an object of the present invention to provide an implant that can function as a carrier for biologically active agents (i.e. chemotactic substances) or other osteoinductive/osteogenic agents, as well as other therapeutic substances (i.e. antibiotics);

16) It is an object of the present invention to provide an implant that can resorb or degrade (at least partially) in several stages to allow for new tissue in-growth and to eliminate the need for second surgeries to remove the implant; and, 17) It is an object of the present invention to provide an implant that can utilize native fibrous collagen to provide structural integrity to the implant and serves as an ideal substrate for tissue regeneration.

To that end, a preferred embodiment of the treatment system comprises a delivery instrument and an implant. The implant may comprise one or more biocompatible materials for introduction into the bone or other tissue to be treated. The delivery instrument is arranged to introduce the implant at or adjacent to the targeted tissue, whereupon the implant directly enters the targeted tissue at an entry situs.

BRIEF DESCRIPTION OF THE DRAWINGS

FIG. 1 illustrates in plan view the tissue treatment system 10 of the present invention, partly cut away to show in cross-section its constituent components, including a sheath, an applicator plunger and a preloaded implant disposed within the sheath.

FIG. 2A is a perspective view of one embodiment of the implant of the subject invention.

FIG. 2B is a perspective view of an alternative embodiment of the implant of the subject invention.

FIG. 2C is a perspective view of an alternative embodiment of the implant.

FIG. 2D is a perspective view of an alternative embodiment of the implant.

FIG. 2E is a perspective view of an alternative embodiment of the implant.

FIG. 2F is a perspective view of an alternative embodiment of the implant.

FIG. 10 is a side elevational view of an alternate treatment and delivery system 110 of the subject invention.

FIG. 11 illustrates a side elevational view of a tissue treatment system 110 of the present invention, modifying the tissue of the living being.

FIG. 12 illustrates a side elevational view of the tissue treatment system 110 of the present invention, shown removing a core of tissue from a living being.

FIG. 13 illustrates a side elevational view partially in section of a tissue treatment system 110 of the present invention, delivering an implant into tissue of a living being.

DETAILED DESCRIPTION OF PREFERRED EMBODIMENTS

Figure 2G:
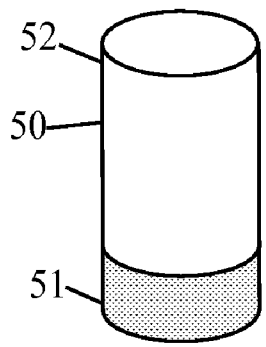
FIG. 2G is a perspective view of an alternative embodiment of the implant.

A preferred embodiment of current invention essentially consists of an implant comprising a tissue (e.g., bone, cartilage, soft tissue, etc.) substitute material and a method and system for deploying the implant. In general the implant of this invention is generally fabricated from one or more biocompatible materials (e.g. polymer, metal, ceramic) that will act to treat the wound and serve as a scaffold for the in-growth of tissue. The implant may contain a depot of material (e.g. calcium salts, collagens, cytokines, drugs, etc.) for assisting the in-growth of cells and act as a carrier for other constituents (e.g., see tables 2 through 7, and accompanying discussion, etc.) of the invention which act to beneficially treat the living being in which they are implanted. Some embodiments of the invention also incorporate cells or other biological constituents for providing the basic building blocks for tissue regeneration.

Many materials can be used to construct the implant, or a portion thereof, of our invention. Biocompatible polymers (e.g., collagen, chitosan, alginate, polylactide-co-glycolide, polyurethane, polyethylene) are preferred for use in this invention. As will be described later, collagen, and most specifically native fibrous collagen, is a preferred constituent of the implant. Additionally, biocompatible resorbable synthetic polymers may be used, such as, but not limited to, those listed in table 1. However, virtually any biodegradable and/or biocompatible material may be used with the present invention.

In the art, there exists three general classes of collagen that are typically useful as medical implant materials. These include collagen-based implants comprised of soluble collagen, reconstituted collagen fibers, or natural insoluble collagen fibers.

First, "Soluble collagen" refers to the solubility of individual tropocollagen molecules in acidic aqueous environments. Tropocollagen may be considered the monomeric unit of collagen fibers and its triple helix structure is well recognized.

Second, "reconstituted collagen" is essentially collagen fiber segments that have been depolymerized into individual triple helical molecules, then exposed to solution and then re-assembled into fibril-like forms. Therefore, the degree of polymerization of reconstituted collagen is between that of soluble and native insoluble fibrous collagen. A disadvantage of reconstituted collagen is, in general, the mechanical strength and in vivo persistence are inferior to native (i.e. natural) insoluble fibrous collagen.

Third, "Natural insoluble collagen" as used herein means and refers to collagen that cannot be dissolved in an aqueous alkaline or in any inorganic salt solution without chemical modification, and includes for example hides, splits and other mammalian or reptilian coverings. For example, "natural insoluble collagen" can be derived from the corium, which is the intermediate layer of a animal hide (e.g. bovine, porcine, etc.) that is situated between the grain and the flesh sides.

In this embodiment, as well as the balance of the specification and claims, the term "bioabsorbable" is frequently used. There exists some discussion among those skilled in the art, as to the precise meaning and function of bioabsorbable material (e.g., polymers), and how they differ from resorbable, absorbable, bioresorbable, biodegradable, and bioerodable. The current disclosure contemplates all of these materials, and combines them all as bioresorbable; any use of an alternate disclosed in this specification is meant to be inclusive of the others.

TABLE 1

Examples of Additional Biodegradable Polymers for Use in Construction of the Matrix of this Invention Aliphatic polyesters
Cellulose
Chitin
Collagen
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/$\epsilon$-caprolactone copolymers
Lactide/$\sigma$-valerolactone copolymers
L-lactide/dl-lactide copolymers
Methyl methacrylate-N-vinyl pyrrolidone copolymers
Modified proteins
Nylon-2
PHBA/$\gamma$-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)
Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-$\beta$-hydroxypropionate (PHPA)
Poly-$\beta$-hydroxybutyrate (PBA)
Poly-$\sigma$-valerolactone
Poly-$\beta$-alkanoic acids
Poly-$\beta$-malic acid (PMLA)
Poly-$\epsilon$-caprolactone (PCL)
Pseudo-Poly(Amino Acids)
Starch
Trimethylene carbonate (TMC)
Tyrosine based polymers As described previously, one of the preferred constituent materials of the device is collagen, or more specifically native fibrous collagen. One embodiment of the present invention combines two or more forms of collagen to create a unique composite material with multi-phasic properties. A mechanically stable, conformable collagen-based implant is fabricated by lyophilizing (freeze-drying) a specialized collagen suspension of native insoluble collagen fibers suspended in a soluble collagen slurry of desirable viscosity. In the preferred embodiment the ratio of soluble to insoluble fibrous collagen is maintained in the range of about 1:20 to 10:1, and the resulting product is compressed to a volume between about 5 and 95 percent of its starting volume. However, other ratios of constituent materials or compressive levels can be utilized depending upon the desired result. The material may be treated with optional physical crosslinking techniques (e.g. dehydrothermal, gamma radiation, ethylene oxide, or ultraviolet radiation) known in the art. Chemical crosslinking methods can be utilized where the addition of chemical crosslinking agents, whose residual elements may inhibit the healing process, does not produce deleterious effects. Implants prepared in such a fashion demonstrate high absorptivity, i.e., about 5-20 times its weight in isotonic saline, making it highly useful as a carrier for other agents (e.g., drugs, biologics, cells, etc.). The implant may then be coated, impregnated or combined with a variety of other materials to enhance mechanical or healing properties.

Because the collagen suspension of the preferred embodiment of the present invention contains both soluble and insoluble collagen, the soluble collagen and insoluble collagen fibers are first prepared separately, then combined. Both the soluble collagen and the natural insoluble collagen fibers ("native collagen fibers") in accordance with the present invention are preferably derived from bovine hides but can be prepared from other collagen sources (e.g. bovine tendon, porcine tissues, recombinant DNA techniques, fermentation, etc.).

To create a multi-phasic implant for example, the soluble and fibrous collagen can be lyophilized and subsequently optionally crosslinked to produce a mechanically stable and porous collagen structure. Compression of the collagen sheet renders the construct less porous and effectively increases the density of the implant. When implanted, the soluble collagen will degrade faster than the native fibrous collagen. The soluble collagen will thus act like a delayed "porosifying" agent, and the plug will become more porous after implantation. The effective density of the implant material will change, possibly as soon as the first few days, following implantation to be receptive for optimal cellular infiltration. For example, the plug will thus be more conducive to cellular infiltration and attachment to the remaining fibrous collagen scaffold, which is important for bone regeneration to occur.

In yet another embodiment, a portion of the implant of the present invention can also be formed of a synthetic polymer material (e.g. PTFE, polylactic-co-glycolic acid, etc.). U.S. Pat. No. 5,683,459 (Brekke), assigned to the same entity as the present invention and hereby incorporated by reference, describes methods and apparatus for treating bone deficiencies with polymer based devices.

The device of the subject invention (e.g. implant, delivery system) may contain or deliver one or more biologically active or pharmaceutical agents (i.e., therapies), such as but not limited to those disclosed in Table 2.

TABLE 2

Examples of Biological, Pharmaceutical, and other Active Ingredients Deliverable via the Present Invention Adenovirus with or without genetic material
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
    Erythromycin
    Penicillin
Anti-coagulants
    Heparin
Anti-growth factors
Anti-inflammatory agents
    Dexamethasone
    Aspirin
    Hydrocortisone
Antioxidants
Anti-platelet agents
    Forskolin
Anti-proliferation agents
Anti-rejection agents
    Rapamycin
Anti-restenosis agents
Antisense
Anti-thrombogenic agents
    Argatroban
    Hirudin
    GP IIb/IIIa inhibitors
Anti-virus drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells
    Bone marrow cells
    Blood cells
    Stem Cells
    Umbilical cord cells
    Fat cells
    Bone cells
    Cartilage cells
Chemotherapeutic agents (e.g. Ceramide, Taxol, Cisplatin)
Cholesterol reducers
Chondroitin
Collagen Inhibitors
Colony stimulating factors
Coumadin
Cytokines prostaglandins
Dentin
Etretinate
Genetic material
Glucosamine TABLE 2-continued Examples of Biological, Pharmaceutical, and other Active
Ingredients Deliverable via the Present Invention Glycosaminoglycans
GP IIb/IIIa inhibitors
    L-703,081
Granulocyte-macrophage colony stimulating factor (GM-CSF)
Growth factor antagonists or inhibitors
Growth factors
    Acidic fibroblast growth factor (aFGF)
    Autologous Growth Factors
    Basic fibroblast growth factor (bFGF)
    Bone morphogenic proteins (BMPs)
    Bovine Derived Growth Factors
    Cartilage Derived Growth Factors (CDF)
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived endothelial cell growth factor (PD-ECGF)
    Platelet Derived Growth Factor (PDGF)
    Recombinant NGF (rhNGF)
    Recombinant Growth Factors
    Tissue Derived Cytokines
    Tissue necrosis factor (TNF)
    Transforming growth factors alpha (TGF-alpha)
    Transforming growth factors beta (TGF-beta)
    Tumor necrosis factor alpha (TNF-.alpha.)
    Vascular Endothelial Growth Factor (VEGF)
    Vascular permeability factor (UPF)
Growth hormones
Heparin sulfate proteoglycan
HMC-CoA reductase inhibitors (statins)
Hormones
Erythropoietin
Immoxidal
Immunosuppressant agents
inflammatory mediator
Insulin
Interleukins
Interlukin-8 (IL-8)
Interlukins
Lipid lowering agents
Lipo-proteins
Low-molecular weight heparin
Lymphocytes
Lysine
MAC-1
Morphogens
Nitric oxide (NO)
Nucleotides
Peptides
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Steroids
Sulfonyl
Thrombin
Thrombin inhibitor
Thrombolytics
Ticlid
Tyrosine kinase Inhibitors
    ST638
    AG-17

TABLE 2-continued

Examples of Biological, Pharmaceutical, and other Active
Ingredients Deliverable via the Present Invention Vasodilator
    Histamine
    Forskolin
    Nitroglycerin
Vitamins
    E
    C
Yeast Regardless of the time of investment or incorporation of these therapies, they may be in solid particulate, solution gel or other deliverable form. Utilizing gel carriers may allow for the materials to be contained after wetting, for some tailorable length of time. Furthermore, additions may be incorporated into the macrostructure during manufacture, or later. The incorporations may be made by blending or mixing the additive into the macrostructure or microstructure material, by injection into the gel or solid material, or by other methods known to those skilled in the art. Another method of incorporating additives, biologics and other therapies, into the macrostructure or microstructure of one or more regions of the device is through the use of microspheres.

The term "microsphere" is used herein to indicate a small additive that is about an order of magnitude smaller (as an approximate maximum relative size) than the implant. The term does not denote any particular shape; it is recognized that perfect spheres are not easily produced. The present invention contemplates elongated spheres and irregularly shaped bodies.

Microspheres can be made of a variety of materials such as polymers, silicone and metals. Biodegradable polymers are ideal for use in creating microspheres (e.g., see those listed in tables 2 and 3). The release of agents from bioresorbable microparticles is dependent upon diffusion through the microsphere polymer, polymer degradation and the microsphere structure. Although most any biocompatible polymer could be adapted for this invention, the preferred material would exhibit in vivo degradation. Upon review of the present disclosure, those skilled in the art will recognize that there can be different mechanisms involved in implant degradation like hydrolysis, enzyme mediated degradation, and bulk or surface erosion. These mechanisms can alone or combined influence the host response by determining the amount and character of the degradation product that is released from the implant. The most predominant mechanism of in vivo degradation of synthetic biomedical polymers like polyesters, polyamides and polyurethanes, is generally considered to be hydrolysis, resulting in ester bond scission and chain disruption. In the extracellular fluids of the living tissue, the accessibility of water to the hydrolyzable chemical bonds makes hydrophilic polymers (i.e. polymers that take up significant amounts of water) susceptible to hydrolytic cleavage or bulk erosion. Several variables can influence the mechanism and kinetics of polymer degradation, e.g., material properties like crystallinity, molecular weight, additives, polymer surface morphology, and environmental conditions. As such, to the extent that each of these characteristics can be adjusted or modified, the performance of this invention can be altered.

In a homogeneous embodiment (i.e., monolithic or composite of uniform heterogeneity) of a therapy delivering implant material, the device provides continuous release of the therapy over all or some of the degradation period of the device. In an embodiment incorporating microspheres, the therapy is released at a preferential rate independent of the rate of degradation of the matrix resorption or degradation. In certain applications it may also be necessary to provide a burst release or a delayed release of the active agent. The device may also be designed to deliver more than one agent at differing intervals and dosages, this time-staged delivery also allows for a dwell of non-delivery (i.e., a portion not containing any therapy), thereby allowing alternating delivery of non-compatible therapies. Delivery rates may be affected by the amount of therapeutic material, relative to the amount of resorbing structure, or the rate of the resorption of the structure.

Time-staged delivery may be accomplished via microspheres, in a number of different ways. The concentration of therapeutic agent may vary radially, that is, there may be areas with less agent, or there may be areas with no agent. Additionally, the agent could be varied radially, such that one therapy is delivered prior to a second therapy—this would allow the delivery of noncompatible agents, with the same type of sphere, during the same implant procedure. The spheres could also vary in composition among the spheres, that is, some portion of the sphere population could contain one agent, while the balance may contain one or more alternate agents. These differing spheres may have different delivery rates. Finally, as in the preceding example, there could be different delivery rates, but the agent could be the same, thereby allowing a burst dose followed by a slower maintained dose.

As will be described in greater detail later, the agent may be any substance such as a therapeutic agent or enzyme. The agent is preferably a protein such as a degradation enzyme, cytokine or cytokine inhibitor and more preferably a growth factor. As will be appreciated by those skilled in the art, combinations of agents may be used and these agents may be derived form a variety of sources, synthetic and natural and may include recombinant methods of manufacture. The amount of bioactive agent in the implant may be adjusted to achieve the desired dosage. Preferable, the implant material contains between about 0.01 ng and about 300 mg of the active agent per milliliter of implant material. The device could contain more or less depending upon the application for which the device is intended and the required activity level of the selected agent. The agent can be contained within the implant in a number of methods known to those skilled in the art.

The term "therapy" has been used in this specification, in various instances; notwithstanding these various uses, many in combination with other agents (e.g., drug, biologic, agent, biologically active agents, etc.), therapy is not meant to be exclusive of these, but rather to incorporate them, and vice-versa. The usage herein is employed to be more descriptive of potential treatment forms, and not limiting as to the definition of the term. Additionally, "biologically active agents" may be relatively inert, but may cause a response by their taking up space, or causing tissue strain or separation.

In yet another embodiment, the implant may incorporate microparticles (e.g. microspheres) dispersed throughout its structure to deliver a therapeutic agent. As is known in the art, microspheres are well known for their use in long term controlled release of drugs or other beneficial agents. This is a highly developed technology that has been used in many applications and such microspheres are available from a variety of sources (e.g., Polymicrospheres, Indianapolis, Ind.). The microsphere structures typically consists of: (a) a continuous drug phase surrounded by a continuous barrier membrane or shell (microcapsule), (b) a shell structure where the drug phase is subdivided into numerous domains scattered uniformly through the interior of the microsphere, (c) a polymer matrix throughout which the drug is uniformly dispersed, (d) a structure where the drug is either dissolved or molecularly dispersed within the carrier material from which the microsphere is prepared, or (e) homogeneous solid. The most common method of delivering drugs or other therapeutic agents with microspheres incorporates these agents uniformly within a polymer matrix, additionally this embodiment contemplates radially non-uniform spheres arranged to provide time-staged delivery of therapies.

The subject invention can also incorporate cellular additions. Cellular material may be delivered in combination with or independent of drug delivery. The cellular material may be present on the inside of the implant, outside of the implant, or incorporated within the implant in a porous construct, laminate or other such embodiment. The cellular material may be added to the implant immediately prior to insertion into the body of the living being or may be grown on the implant in the days or weeks prior to implantation so more mature cells are in place when the device is implanted. If the cells are seeded on the implant several days or weeks prior to implantation, the implant may be placed in an in-vitro setup that simulates the in-vivo environment (e.g., where blood or a blood substitute medium is circulated at appropriate pressure and temperature) to acclimate the cells to the intravascular environment. The cell-seeded implant may be incubated in this in-vitro setup at physiologic conditions for several days prior to implantation within the body. Cell seeding techniques have been developed for a variety of cell types. Examples of cellular material that may be seeded on implant are listed in the following Table 3.

TABLE 3

| Cellular Material Deliverable Via this Invention |
| --- |
| Adipose cells |
| Blood cells |
| Bone marrow |
| Cells with altered receptors or binding sites |
| Endothelial Cells |
| Epithelial cells |
| Fibroblasts |
| Genetically altered cells |
| Glycoproteins |
| Growth factors |
| Lipids |
| Liposomes |
| Macrophages |
| Mesenchymal stem cells |
| Progenitor cells |
| Reticulocytes |
| Skeletal muscle cells |
| Smooth muscle cells |
| Stem cells |
| Vesicles |

It is also conceived that a source of cytokines or growth factors (e.g. platelet-rich plasma, bone marrow cells, etc.), whether synthetic, autologous or allograft in origination, can be delivered with the device of this invention (e.g. incorporated into the implant or delivered via the delivery system). For example, it is known that one of the first growth factors to initiate the cascade leading to bone regeneration are platelet-derived growth factor (PDGF) and transforming growth factor-beta (TGF-$\beta$). Each of these growth factors is derived from the degranulation of platelets at the wound, defect or trauma site. It is believed that increasing the presence of such platelets at the wound or trauma site can increase the rate of healing and proliferation needed to regenerate bone.

The application of platelet-rich plasma (PRP) or other autologous blood components is one way to deliver a highly concentrated dose of autologous platelets. PRP is easily prepared by extracting a small amount of the patient's blood and processing it, for example using gradient density centrifugation, to sequester and concentrate the patient's platelet derived growth factors. Other preparation methods remove water from the buffy coat and utilize filtering systems to concentrate platelets and fibrinogen. It is believed that applying PRP or other autologous growth factors to the wound site in conjunction with the subject invention will increase the amount of PDGF and TGF-β available for jump-starting the healing process. PRP can be prepared for procedures with small volumes of blood, drawn by the doctor or nurse pre-surgically. Typically, 40-100 ml of blood are drawn preoperatively and placed in a PRP preparation unit. SmartPREP (Harvest Technologies Corp., Norwell, Mass.) and UltraConcentrator (Interpore Cross, Irvine, Calif.) are device that have been shown to effectively produce PRP for OR, office implant, and periodontal uses.

Once the PRP is prepared, other additives (e.g. activator, growth factor, drug, chemical, bone, etc.) can be added to the plasma. For example, an activator can be used to gel the PRP material prior to application to the implant device or delivery to the surgical site. One such activator includes 5 ml of 10% calcium chloride with 5,000 units of topical bovine thrombin (GenTrac, Middleton, Wis.). Depending upon the flowability of the PRP, the type and quantity of activator can be adjusted. For example, to infuse the implant material of this invention with a PRP gel preparation, the ratio of ingredients would include a higher proportion of PRP to allow the PRP to more effectively flow through and permeate through the porous implant material. It is also conceived that the implant material (e.g. cylinder or other biomaterial implant) can be inserted into the PRP preparation unit (e.g. centrifuge, concentration unit). In this fashion, the platelets can be concentrated right into or onto at least a portion of the implant directly. For example, some PRP devices include a centrifuge for separation of the blood components. The biomaterial implant could be positioned within the centrifuge such that the desired blood constituent is directed into the implant material during processing.

The advantages of an autologous growth factor application such as PRP would be twofold. First, the significant fibrin and fibronectin components of the PRP enhances cell adhesion and induces osteoconduction by providing a structure onto which precursor cells can migrate and bone can grow. Second, it amplifies the influence of PDGF and TGF-β, which are formed as the platelets degranulate. The addition of exogenously delivered amounts of highly concentrated PDGP and TGF-β promotes an amplified cascade that results in increased cellular population and subsequent expression of more growth factors. This benefit can play a role in the healing process and can lead to more rapid and effective tissue regeneration. This may be attributed to the concentrated levels of fibrin, PDGF, TGF-β, as well as other growth factors or proteins that have not as yet been identified.

Other autologous materials can also be incorporated into and or used in conjunction with the subject invention (e.g., autologous bone marrow cells (BMC)). Bone marrow contains osteogenic progenitor cells that have the ability to form and repair bone. The marrow can be harvested and dispersed into single cell suspensions. The cells can then be concentrated (e.g. through filtering, centrifugation) or used as is. The resulting mixture can be diluted and implanted into the wound site, incorporated into the implant material, or delivered by the delivery system of the subject invention.

The use of growth factors such as PRP or progenitor cells from BMC are particularly beneficial for patients with risk factors that typically reduce the success of bone grafts and osteointegration, including the edentulous, severely atrophic maxilla, and patients with osteoporosis. Combining growth factors and progenitor cells with absorbable delivery systems could result in significant changes in the outcomes we can expect for guided tissue regeneration.

There are many other materials which can be used to construct the implant or a portion thereof. Table 4 below lists some of the possible materials which can be used either as fillers or as the main construct. This list is not complete but is only presented to as a non-limiting example of some of the materials which may be used for this invention.

TABLE 4

Examples of Materials Suitable for Filler or for the Main Construct of the Present Invention Alginate
Calcium
Calcium Phosphate
Calcium Sulfate
Ceramics
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium In addition to pure polymer materials, additives may be combined with the polymers to improve their mechanical, biological, or resorption characteristics. One example of additives would be plasticizers which can alter the mechanical performance of polymers to make them more elastic or deform more plastically. Another additive may be nanoparticles which increase the strength and may change the resorption properties of polymers. Additives can be incorporated into the polymers with standard melt compounding, solvent mixing, or other processes known in the art. Examples of plasticizers and nanoparticles are shown in, but not limited to, Tables 5 and 6.

TABLE 5

Polymer Plasticizers which may be Useful in the Present Invention

- 1,2-cyclohexadione
- Acetoxytriethyl citrate
- Acetylated coconut oil (EPZ)
- Acetyltri-n-butyl citrate
- Acetyltri-n-hexyl citrate
- Actyltriethyl citrate
- Adipate esters
- Benzoic acid-2-hydroxyacetate
- Bis-2-methoxyethyl phthalate
- Calcium stearate
- Camphor
- Caprolactone
- Citrate esters
- Dibutylphthalate
- Diethyl phthalate
- Dioctyl adipate
- Epoxidized soy oil
- Ethyl benzoate
- Ethyl-, butyl-, and hexyl-esters of acetylated citric acid
- Ethyl-terminated oligomers of lactic acid
- Glycerol
- Glyceryl triacetate
- Glycolide
- Hexamethylbenzene
- Lactide
- Linseed oil
- Lipids
- Liposomes
- n-Butyryltri-n-hexyl citrate
- Oil
- Pthallic esters
- Polyurethane
- Stearic acid
- Tributyl citrate
- Triethyl citrate

TABLE 6

Nanoparticles

- Silica
- Clay
- Metals
- Aluminum Oxides
- Ceramics
- Polymers
- Metal Oxides

When implanting a material into the tissue of a living being (e.g. for the purpose of treating a wound or defect) it is generally important that the implant is physically and chemically compatible with the host tissue. "Integrity matching," as used herein, refers to processing that alters the strength of the implant, such that the resulting strength matches or nearly approximates the strength of the organic host tissue. Porosity matching refers to processing that alters the pore structure (i.e., size, shape, and/or population), in the implant, such that the resulting porosity matches or nearly approximates the pore structure of the organic host tissue. Compliance matching refers to compressive processing that tailors the implant compliance (e.g., modulus and/or coefficient of restitution, etc.) such that it matches or nearly approximates the compliance of the organic host tissue. Structure matching refers to any process utilized to create a structure similar to the host tissue (e.g., fibrous nature or other heterogeneities). Weight matching refers to processing that alters the molecular weight of the implant's matrix, such that the resulting molecular weight matches or nearly approximates the molecular weight/structure of the organic host tissue. Separately, together, or in any combination, these "matching" processes are referred to as bio-matching; said bio-matching processes being utilized to create a "bio-matched" implant.

A portion of the implant of one bio-matched embodiment of this invention can be formed of a ceramic material such as calcium phosphate, calcium carbonate and calcium sulfate or other derivates. Examples of products constructed of these materials include Wright Medical Technology's Osteoset™ (Arlington, Tenn.), BioGeneration's ProFusion™ (Arlington, Tenn.), Encore's Stimulan™ (Austin, Tex.), Norian Corporation's SRS™ (Cupertino, Calif.), and Interpore Cross' ProOsteon™ (Irvine, Calif.).

There are numerous ceramic systems that display both biocompatability and degradability. In the body, the bone itself is the natural storehouse of minerals. The major mineral component of bone is hydroxyapatite, a form of calcium phosphate. Other calcium phosphate salts in bone include monotite, brushite, calcium pyrophosphate, tricalcium phosphate, octocalcium phosphate, and amorphous calcium phosphate. Additionally, bone contains calcium carbonates. Hydroxyapatite and tricalcium phosphate are the most widely studied of the calcium phosphates, which have calcium to phosphate ratios of between 1.5 to 1.67 respectively. Calcium phosphate, $Ca_{10}(PO_4)_6(OH)_2$, is known as a physiologically acceptable biomaterial which is useful as a hard tissue prosthetic. Another calcium mineral used as a bone replacement material is calcium sulfate. Most of the calcium-based biomaterials can be molded under high pressure, thereby effecting integrity and strength. Pores may be useful to assist host matrices in osteoconduction, and pores may be formed in molded calcium phosphate by compaction of calcium phosphate powders containing naphthalene followed by removal of the naphthalene by leaching or sublimation. Hydrothermal exchange of marine coral structures (i.e., calcium carbonate for calcium phosphate), and decomposition of hydrogen peroxide are other methods to generate a pore-filled structure. The dense forms of the calcium phosphate implant have mechanical properties equal to or exceeding that of natural bone, but their porous forms typically do not. Certain processing steps, such as these, and others known to those skilled in the art, may be used to tailor the physical and mechanical properties of the resulting implant.

In addition to drugs and biologics, coatings may be added to the implant to enhance the performance of the device. The coating may increase lubricity for improved insertion, increase thrombogenicity to promote hemostasis and platelet deposition, or provide other advantages to the implant. The coating may also be used as a mechanical barrier to protect underlying cellular material which may be incorporated onto the implant material to work in concert with the agent delivery aspects of the invention. Examples of possible coating materials are listed in Table 7.

Additionally, an embodiment of the current invention may comprise a calcium salt and a native-collagen matrix. This may be accomplished by first forming a specialized collagen suspension of native insoluble collagen fibers suspended in a soluble collagen slurry of desirable viscosity, in which the ratio of soluble to insoluble fibrous collagen is maintained in the range of about 1:20 to 10:1. Into this slurry is added a calcium salt such as calcium sulfate. Enough calcium salt should be added to the slurry to ensure that the final product will have the desired weight percentage of calcium salt, between about 10% and 90%. The final product can be made in a number of methods. In one such method, the solution is fully homogenized and poured into molds or large sheets of the desired shape or thickness, and it is recognized that there exists other techniques known in the art that should prove sufficient for these applications. The product is then lyophilized in the manner described previously. The material thus produced may also be treated with optional crosslinking treatments (e.g. chemical, dehydrothermal, gamma radiation, ethylene oxide, or ultraviolet radiation) as will be understood by those skilled in the art upon review of the present disclosure.

TABLE 7

Example Materials for Use in Coating the Present Invention

Albumin
Alkyl methlacrylates
Glycosaminoglycans
Heparin
Hyaluronic acid
Hydrophilic polymer
Integrins
Paralyne
Phosphorylcholine
Phospholipids
Polyacrylamide
Polyanhydrides
Polyethylene acetate
Polyethylene glycol
Polyethylene oxide
Polypeptides
Polyurethane
Polyvinyl alcohol
Polyvinyl pyrrolidone
Silanes
Silicone The implants of the present invention are placed within the tissue to enhance or stimulate healing. Also, by combining the use of these implants with other surgical devices such as sutures, screws, pins and rods, the effectiveness of tissue repair can be greatly enhanced (e.g. serve as a site for attachment of a second tissue).

The subject invention can be utilized to repair or treat wounds in a variety of tissues. Tissue is typically described as an aggregation of similarly specialized cell united in the performance of a particular function. The implant structure and material can be manipulated (integrity matched) so as to closely approximate the mechanical properties (e.g., stiffness, compressibility) matching the surrounding tissue. Implant materials can be designed to match the mechanical properties of bone, cartilage, tendon, skin, ligament, arteries, etc. As a non-limiting example, the device can be utilized to treat or heal defects in bone. Bone is a unique connective tissue with a hard extracellular collagen matrix that is impregnated with a mineral, principally hydroxyapatite. In general, there are two forms of bone tissue: cortical and cancellous as will be described later.

There are many other tissues that can be repaired using the implant or a portion thereof. Table 8 below lists some of the possible tissues and procedures that can use this invention. This list is not complete but is only presented to as an example of some of the tissues or procedures which may be used for this invention.

TABLE 8

Examples of Tissues and Procedures Potentially
Benefiting from the Present Invention Bone
Bone tissue harvest
Spinal arthrodesis
Spinal fixation/fusion
Osteotomy TABLE 8-continued Examples of Tissues and Procedures Potentially
Benefiting from the Present Invention Bone biopsy
Maxillofacial reconstruction
Long bone fixation
Compression fractures
Hip reconstruction/replacement
Knee reconstruction/replacement
Hand reconstruction
Foot reconstruction
Ankle reconstruction
Wrist reconstruction
Elbow reconstruction
Shoulder reconstruction
Cartilage
Mosaicplasty
Meniscus
Dental
Ridge augmentation
Third molar extraction
Tendon
Ligament
Skin
Topical wound
Burn treatment
Biopsy
Muscle
Dura
Lung
Liver
Pancreas
Gall bladder
Kidney
Nerves
Artery
Bypass Surgery
Cardiac catheterization
Heart
Heart valve replacement In a time-phased delivery embodiment, the implant may be constructed to effect a tailored delivery of active ingredients. Both the presence of the implant and delivery of the select agents is designed to lead to improvements in patients with tissue defects, as a result of delivering in no certain order: (1) a substratum onto which cells can proliferate, (2) a drug or biologic which can act as a signaling molecule which can activate a proliferating or differentiating pathway, (3) a drug or biologic which may act as a depot for nutrients for proliferating and growing cells, and (4) a drug or biologic which will prevent an adverse tissue response to the implant, or provide a therapy which reduces infection and/or treats an underlying disease or condition.

Referring now to the drawings, FIG. 1 illustrates one of the preferred embodiments of a tissue defect treatment system 10 of the present invention. As shown in FIG. 1, tissue defect treatment system 10 generally comprises a sheath 12, a mass of implant material 14 and an applicator 16. The treatment system is suitable for open, laparoscopic, arthroscopic, endoscopic and other surgical procedures known for treating a variety of injuries or maladies.

Sheath 12 generally comprises a tubular housing 18 defining a lumen 19, a hub 20 disposed at the proximal end of housing 18, and an outlet 13 at the distal end. The hub 20 is provided, at its proximal end, with a flange 21, which is designed to serve as a finger grip. The treatment system 10 can be rigid or flexible depending upon the application. The sheath 12 or applicator 16 may be lubricated to reduce friction or otherwise ease the placement of the implant material. It may also be desirable to provide a tubular housing 18 fabricated from a transparent material such as Lexan™ for purpose of visualizing the delivery of implant material 14 through the tubular housing 18. In general, the tubular housing 18 is an elongated member preferably constructed of a sufficiently small outside diameter, e.g., 5 mm to 10 mm, and somewhat flexible pliable biocompatible material suitable for use in surgical procedures (e.g., a gamma-sterilizable material), and is preferably composed of a durable plastic material such as Teflon, polyethylene or polyurethane or possibly a metal.

When required for an arthroscopic procedure, the outer diameter and cross-sectional configuration of housing 18 are chosen so as to permit sliding passage, with minimal clearance, through the channel of a laparoscopic cannula (e.g. trocar) or incision. In a preferred embodiment, the sheath is circular in cross-section, with the outer diameter being in the range of between about 3 to about 10 mm. These dimensions are generally suitable for existing laparoscopic or endoscopic cannula. The actual sizing, however, will vary depending on the procedure and circumstance, as will be readily appreciated by those skilled in the art.

Applicator 16 basically comprises an elongated, cylindrical rod-like plunger 22 having a thumb plate 24 disposed at its proximal end and having a distal end 15. Plunger 16 will generally be fabricated of a pliable biocompatible material suitable for use in surgical procedures (e.g., a gamma-sterilizable material), and is preferably composed of a plastic material, such as polypropylene, polycarbonate, or polyethylene. The sizing of the outer diameter of plunger 22 is selected so that it has a cross-section and configuration that permits sliding passage with minimal clearance through lumen 19 of tubular housing 18 to push or force the implant 14 through the outlet 13.

In order to effectuate the movement of the pusher from the retracted to the extended position, the tubular housing 18 includes a collar having a flanged projection 21 arranged to be grasped by the fingers of the user of the device 10. In addition, the proximal end of the applicator 16 includes an enlarged cap 24 arranged to be engaged by the user's thumb. Thus, to effect the ejection of the implant 14, the user of the device 10 merely has to grasp the projection 21 with his/her fingers while applying pressure to the cap 24 with his/her thumb. This action forces the pusher down the tubular body to the extended position thereby ejecting the implant 14. Thus, the applicator 16 is arranged to be moved from a retracted position, like that shown in FIG. 1, to an extended position, like that shown in FIG. 8, wherein its distal end 15 is located close to the outlet 13 of the tubular housing 18 (e.g. the length of plunger 22 is selected so that when thumb plate 24 abuts finger grip 21 of hub 20, the distal end of plunger 22 will align with the distal end of sheath 12). In a preferred embodiment, plunger 22 is composed of a solid plastic material with a blunt distal end for engaging and advancing implant material 14 through and out of sheath 12.

Preferably, the implant 14 is preloaded in the delivery system prior to the latter's insertion into the patient's body. The implant 14, for solid or rigid implant materials (e.g., not readily flowable) is sized so that the fit between the implant and the inside of tubular housing 18 is such that the implant will not inadvertently drop out of the sheath unless advanced by the plunger 22. If necessary, a looser or tighter fit can be provided by adjusting the size of the implant or the internal diameter of the sheath 12.

Alternatively, a number of methods could be used to retain the implant within the sheath 12 until the device is properly positioned. For example, the distal tip 13 of sheath 12 can be constructed to be deformable to provide valve-like properties (e.g. duckbill valve) that would hold the implant within the delivery system until the implant is advanced by the plunger 22. The deformable tip could be fabricated from elastomers such as polyisobutane (i.e. rubber) or plastics such as polyethylene. A removable cap, a dimpled distal tip, or other retention means could also be used, as well as other methods known to those skilled in the art.

As shown in FIG. 2A, the embodiment of the implant 14 is formed of dense polymer (e.g. collagen) foam with long native collagen fiber reinforcement. The implant is compressed prior to loading into the delivery system so that it has a high expansion ratio (wet-to-dry) and good mechanical wet strength. The implant may contain particles of a calcium derivative such as, but not limited to, calcium sulfate or hydroxyapatite throughout the implant to enhance the healing properties. The open pores of the implant allow body fluids and cells to permeate the implant during the healing process, or to facilitate the healing process. This and other embodiments of the device can be constructed from various polymers as described previously. In general, the gross structure of the devices is composed of biologically acceptable, biodegradable polymer arranged as a one or more piece porous body with interconnecting voids. In some cases it may be desirable that each void communicates with a large proportion of the other voids. Depending upon the application, the voids or pores may be uniformly or randomly sized, positioned and shaped. For example, an implant with an interconnecting, open-cell meshwork, would duplicate the architecture of human cancellous bone from the illiac crest and when fabricated form suitable materials (e.g. polymers) possess physical property (strength) values in excess of those demonstrated by human (mammalian) illiac crest cancellous bone.

FIG. 2B depicts implant 14 after it has expanded in diameter, implant 14E, after being released from the sheath and in response to the body fluids. In the preferred embodiment the implant 14 is a slightly expandable member which can be contracted or compressed compact to fit within the interior of the tubular housing 18, but it changes (e.g., expands) to a configuration suitable for filling and treating the wound or defect in the tissue (e.g., when either unconstrained by the tubular housing, in contact with body fluids, at body temperature, etc.).

As will be described later, the implant can be compressed to any degree to provide for a good fit within the delivery system and the tissue wound. Compression will also increase the effective density and mass of the implant and may be useful for controlling resorption time or post procedure strength (integrity matched). In some cases it may be preferable to provide an implant which is not compressed. In the event that a solid implant is not compressed, a retention cap or retention band can be used to hold the implant 14 within the tubular housing 18 until time for delivery.

As previously described, the implant material 14 may be composed of a wide variety of biocompatible materials, preferably a bioresorbable material (e.g., polymer, collagen), and preferably incorporating native fibrous collagen. The implant material may be in any form, which is suitable for delivery through the treatment system. For example, it may be in the form of a loose fibrous material, (e.g., a cottony or fleece-like material), a sponge, a paste or flowable form, a folded membrane, a woven or non-woven sheet, compressed/fused granules or pellets. As mentioned earlier the implant is preferably formed of a bioresorbable (e.g., biodegradable) material. This feature enables the implant to be left in place until the bodily tissues resorb it thereafter. Accordingly, the implant does not have to be removed after having served its purpose.

While the implant 14 may be composed of any biocompatible material, native fibrous collagen is believed very suitable for at least one of the implant constituents. The physical form of implant 14 may vary widely, with the one selected by the physician being dependent on the circumstances of the case. In alternative embodiments, implant 14 may comprise a combination of one or more types of materials (e.g., collagen, synthetic polymer, and ceramic). The implant 14 may comprise a sponge-like portion and a loose fibrous portion, wherein the loose fibrous portion is disposed at the most distal end of sheath 12. Alternatively, the implant 14 could comprise a flexible portion surrounding a more rigid structural portion. It will be appreciated that this arrangement would first provide a flexible material (e.g. collagen, polymer foam) for intimate contact with the wound site, that is reinforced with a more solid material (e.g. synthetic polymer pin) backing (sponge) for applying pressure over the entire surface of a bleeding site said pressure being the same hydrostatic pressure normally seen at the site (e.g., compliance matched) or somewhat higher. Multiple component implant devices may be joined together or may be structurally separate and independent. Other combinations and their advantages will readily be apparent to those skilled in the art.

In a preferred embodiment, at least a portion of the implant is porous. The pore size can vary depending upon the process by which implant 14 is processed. Preferably, porosity may be more than 50% of the respective structure/material volumetric area. Moreover, pore size can range between 25 and 1000 um. However, it is to be appreciated that pore density as well as pore size can vary outside these ranges depending upon the particular manufacturing process chosen. It may also be desirable to have portions of the implant that are non-porous. Preferably, implant 14 is manufactured having a porosity which generally matches the architecture of the surrounding tissue (e.g., porosity matched or structure matched), into which implant 14 is placed. Thus, depending upon the specific application desired, the method of manufacturing and or the material of implant 14 can be adjusted to contain pores of varying size and population. It is conceivable that the porosity of the implant may change over time. For example, the implant may be fabricated from a porous resorbable polymer macrostructure (U.S. Pat. No. 4,186,448, Brekke) where the pores of the macrostructure are filled with a microstructure material that degrades more rapidly than the porous macrostructure. After implantation, the microstructure may degrade or resorb leaving larger effective porosity. Moreover, implant 14 can be manufactured having architecture and mechanical properties (such as stiffness and compressibility; structure matched, integrity matched or compliance matched, respectively) to substantially match the architecture and/or mechanical properties of surrounding tissue into which implant 14 is placed.

Tissue implant 14, can contain materials of possibly different porosity and/or mechanical properties. As such, the implant can be particularly adapted for placement into a juncture region adjoining tissue areas having dissimilar porosity and/or mechanical properties. The structure and materials of implant 14 correspondingly can be modified to have porosity and mechanical properties such as stiffness, compressibility, etc. to substantially match the properties of the tissue juncture region after implantation (bio-matching), as is discussed and described elsewhere herein.

It should be noted at this juncture that the implant can be of any suitable shape and need not be of the cylindrical-like shaped implant 14 shown in FIG. 2A, so long as it can be effectively placed into position at the situs of the wound. FIG. 2C depicts an alternative embodiment of the implant 40 with a generally cylindrical body 44 and an oversized cylindrical head 42. The cylindrical head can be made of the same material as the body 44 of the implant or of an alternative material. For example, head 44 can be comprised of a more rapidly resorbing material such as soluble collagen. The head could be used to promote hemostasis at the wound site and then rapidly resorb leaving the longer term resorbing cylindrical body 44 in the wound to provide a structural matrix for tissue regeneration. The head 42, or body 40, of implant 40 could also contain select biologics or agents such as thrombin to assist in achieving hemostasis. The head 42 of device 40 could also be used to limit the depth to which the device is implanted. The head 42 could be utilized as an impact surface for hammering the implant into the tissue defect, much like the head of a nail. In this application the head would be fabricated of an appropriately resilient material and could be removable after the device 14 is implanted.

FIG. 2D depicts yet another embodiment of the implant, implant 46 that is constructed in a generally conical fashion. Implant 46 has a tapered tip 47, and a widened base 48. The tapered nature of the implant may allow a better compression fit into the defect site. This implant may be suitable for non-cylindrical (e.g., tapered) defect sites.

Referring now to FIG. 2E, an alternative embodiment to the implant device 14 is shown and designated by the reference number 54. As can be seen, the implant 54 basically comprises a generally elongated structure that is preferably formed of a sheet or film 53 which is reeled up about a mandrel (not shown) to form a tube. The structure could be formed of a lamination of similar sheets to create the final implant device. The tubular member 54 could also be formed of a variety of different materials described herein (e.g., ECM, collagen, polymer, polysaccharide, etc.) in a variety of configurations (e.g., powders, fibers, pellets, spheres, etc.) that can be rolled up or laminated together. For example, by utilizing multiple sheets of different materials the implant could be designed to have varying degradation rates (e.g. multi-stage), varying porosity for tissue in-growth, and staged release of agents or biologics (e.g., thrombogenic drugs, growth factors). It is also conceived that the implant 54 having a central passageway 55 extending longitudinally therethrough for accommodating a guide pin or other guiding element (not shown) that can be used to direct the implant to the desired implant site. The guide element could be removed or left in place. The pin could also extend beyond the distal portion of the implant and serve to stabilize or anchor the implant within the defect site.

Referring now to FIG. 2F, a further alternative embodiment to the implant device 14 is shown and designated by the reference number 56. As can be seen, the implant 56 basically comprises a generally elongated cylindrical structure that is preferably formed of an outer sleeve material 57 and an inner core material 58. Essentially the implant is formed of a rod or bar of material with a longitudinal passageway formed therein in which another material is placed that extends through at least a portion of the rod or bar. Sleeve 57 could be constructed of a hemostatic material to minimize bleeding after placement. Sleeve 57 could also be constructed to resorb more quickly as the surrounding tissue regenerates through its periphery. The inner core 58 could then resorb more slowly to provide a longer term structural substrate for tissue regeneration. It is also conceived that implant 59 could contain an open central passageway extending longitudinally therethrough for accommodating a guide pin or other guiding element (not shown) that can be used to direct the implant to the desired implant site.

Referring now to FIG. 2G alternate implant 50, comprising essentially a compound or composite structure formed of a first structure/material 51 and a second structure/material 52. Although the compound structure embodiment of FIG. 2G is shown with two different constituents, the implant could be fabrication from any number of different elements combined together to achieve a desired result. With respect the FIG. 2G, the first structure/material 51 and second structure/material 52 are preferably made from biocompatible materials. The first structure/material 51 is connected to second structure/material 52, wherein structure/material 14 includes a body having dissimilar materials, therapies (e.g., drugs, biologics) or properties (e.g., mechanical, porosity, wetability) properties from material 12. Both materials 51 and 52 may include therapeutic agents within the pores of the materials or mixed within the structure of the material. Implant 50 can be particularly useful for placement into any physiological system having a juncture between dissimilar types of tissue. Any region joining two dissimilar types of tissue (i.e., bone, cartilage, tendon, skin, ligament, cementum, etc.) can be implanted with the bonded dissimilar structure/materials 51 and 52 of implant 50. By connecting each structure/material together and implanting the combination within a tissue juncture, carrier/implant 10 ensures the tissue juncture remains together during the repair process, which may help to promote rapid healing. It is also conceivable that one portion of a tissue defect may be somewhat more vascularized and prone to bleeding, as such, the compound structure embodiment of FIG. 2G could be designed to have one portion which is comprised of a hemostatic material (e.g. collagen) to help stop bleeding. The materials can be manufactured adjacent to one another during processing (e.g. lyophilization) or can be bonded (e.g., thermal weld, solvent weld, mechanically connected, etc) at a later time.

Figure 2H:
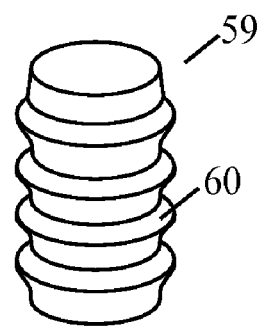
FIG. 2H is a perspective view of an alternative embodiment of the implant.

Referring now to FIG. 2H, which depicts alternate implant 59 comprising essentially a cylindrical structure that has one or more ridges or barbs 60 which can serve to anchor the implant into the tissue and act to prevent the device from being pulled out or dislodged after placement. The ridges or barbs 60 are formed on the outer surface of implant 59. The barb is preferably a circular ridge extending about the circumference of the body. The sharpness or angularity of the barb 60 may be adjusted depending upon the application and the material of the implant. The trailing edge of the barbs grips the sides of a borehole in a bone or other tissue. A blunt tapered tip is formed on the distal end of the body of implant 59. A trailing end of the body of implant 59 is located at the opposite end of the body from the distal end. This embodiment as well as others could also be sutured, stapled, glued or otherwise fixed in position after implantation.

Figure 3:
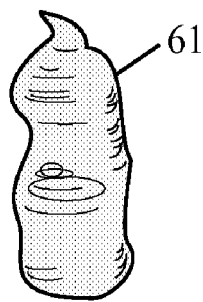
FIG. 3 is a perspective view of an alternative embodiment of the implant.

The embodiment of implant 61 shown in FIG. 3 is a "flowable" implant comprised of a flowable material, such as but not limited to, collagen paste, cyanoacrylate (glue/adhesive), thrombin glue, hydrogel, growth factor gelatin, etc. The flowable material can be stored in a tube (not shown) and dispensed into the tissue defect by a needle-like device, such as a syringe (not shown). The flowable material can be designed to harden slightly after placement, like an epoxy or silicon caulking material, so that it is not extruded from the puncture during tissue movement or flexing. The material could also photopolymerize like FocalSeal (Focal, Inc., Lexington, Mass.). The implant could contain drugs or other agents as described previously. The flowable material could be designed to have porosity by incorporating citric acid, or some other "foaming" agent, that would create pores in the implant during and/or after placement; mixing the foaming agent immediately prior to implant injection would allow foaming to occur primarily following implant, chilling the implant material would also slow the foaming reaction until the implant warmed to body temperature. The implant could also be formed by flowing two or more materials together (e.g. two-part epoxy) into the defect site such that the combination of materials suitably fills the defect site and serves to treat the wound.

Figure 4:
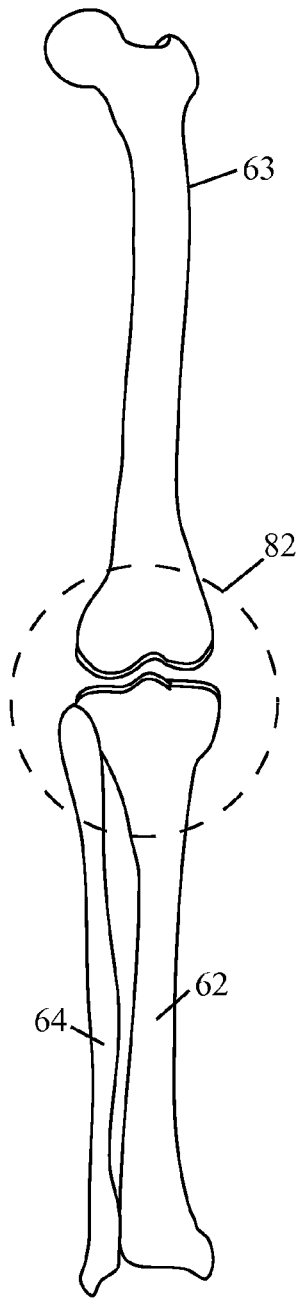
FIG. 4 is a perspective view of one of the various types of tissue that is suitable for treatment by the treatment system of the subject invention.

The implant 14 of this invention is suitable for introduction into a wound, defect or incision in a variety of body tissues or organs (e.g., bone, muscle, artery, dura, lung, liver, gall bladder, etc.). For illustrative purposes, we will describe the use of this device for treating a defect in bone, particularly a defect in long bones. Long bones (bones of the arms and legs) and the vertebrae share many common anatomic and biological structures. FIG. 4 depicts the human femur 63, tibia 62, and fibula 64.

Figure 5:
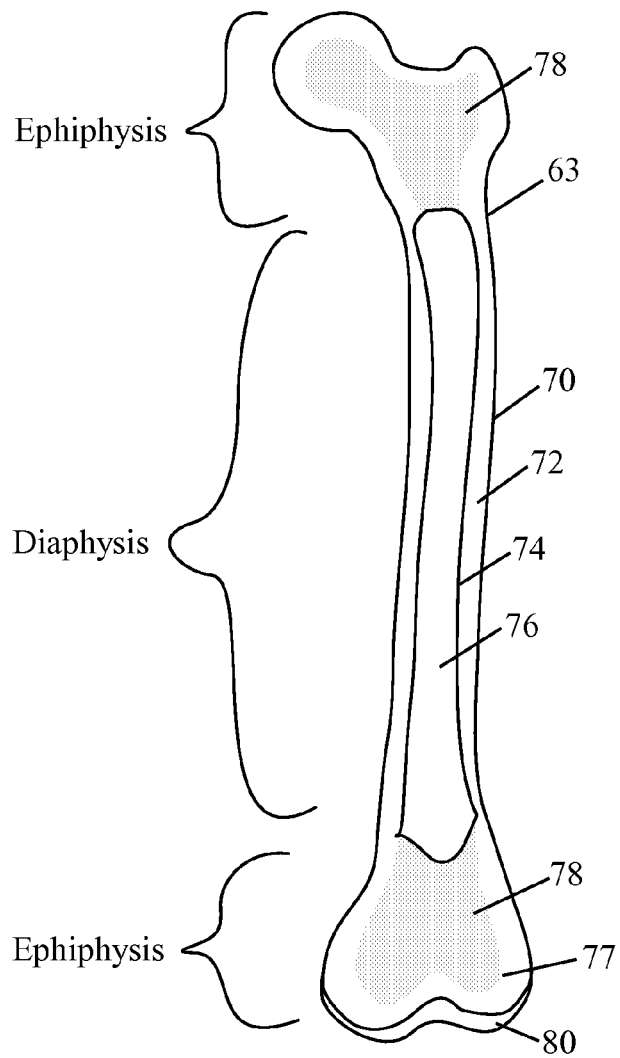
FIG. 5 is a cross-sectional view of tissue from FIG. 4, in partial view, and enlarged.

FIG. 5 depicts a sectional view of femur 63. All long bones (e.g., femur) are composed of a shell of dense, strong tissue encasing a less dense or hollow interior. This construct maximizes strength and minimizes the overall weight, allowing the bones to provide structural support and mobility without encumbering the mobility of the organism. It is important to note that bone is living tissue that contains living cells that must receive oxygen and nutrients from the blood system to survive. At the macroscopic level there are two major forms of bone tissue: compact or cortical; and cancellous or trabecular. The location of these bone types in a femur is illustrated in FIG. 5, and discussed later. Cortical or compact bone is a dense material with a specific gravity of about 2. Cancellous bone tissue, also termed trabecular bone, is a sponge-like, open-celled network of calcified collagen fibers. The fibers of the cancellous bone act like the trusses of a bridge or building construct, providing a lightweight support mechanism for the forces applied to the bone structure.

As shown in FIG. 5, The long bones (bones of the arms, finger, legs and toes) have a hollow shaft, known as the diaphysis, that is capped on each end by a solid bone structure, the epiphysis. The diaphysis is composed of a cylinder of thick cortical 72, or dense, bone that is encased between an outer layer of periosteum 70, and an inner layer of endosteal tissue (the endosteum) 74, the internal counterpart to the periosteum. The periosteal surface is generally very smooth. Like the periosteum 70, the endosteal tissue layer 74 is constructed from a fibrous, leathery structure that provides vascular support for the bone tissue and is rich in osteoblasts, the precursors to osteocytes. It has a roughened texture, which resembles cancellous bone.

Cancellous bone also exists in the epiphysial and metaphyseal region of long bones and within the confines of the cortical bone because it is composed of short struts of bone material called trabeculae. The connected trabeculae give cancellous bone a spongy appearance, and it is often called spongy bone. There are no blood vessels within the trabeculae, but there are vessels immediately adjacent to the tissue, and they weave in and out of the large spaces between the individual trabeculae. Cancellous bone has a vast surface area as would be suggested by its spongy appearance.

The interior of the shaft of a long bone is void of bone tissue. However, this hollow portion, or the medullary canal 76, does contain blood cell-producing red marrow in the fetus and young child. As the need to produce excessive blood cells diminishes, so does the need for the red blood cell-fabricating marrow. The red marrow is eventually replaced by fatty tissue, often called yellow marrow.

The epiphysis comprises a thin layer of cortical bone or articular cartilage 80 (at the articulating surface of the joint) surrounding the lattice structure of bone fibers composing the cancellous bone 78. The periosteum 70 covering the diaphysis extends over the cortical bone region 77 of the epiphysis 78 and coming into contact with the articular cartilage 80.

Cartilage is, in many ways, very similar to bone tissue. Like bone, it consists of a network of fibers in which the cartilage cells, or chondrocytes, are embedded. Unlike bone tissue, the fibers are not calcified, but are embedded with chondroitin sulfate, a gel substance. Also, present in the intercellular space is hyaluronic acid, a viscous material that facilitates the passage of nutrients from the blood vessels to the cells within the matrix. The collagen or elastin fibers in cartilage are arranged in an irregular manner to serve as a surface feature as well as provide compressive strength.

Only approximately 5% of the tissue volume is occupied by chondrocytes, which are not in direct contact with each other. The remaining portion is occupied by the extracellular matrix and the interstitial fluids. There are no vascular, lymphatic, or neural structures in the cartilage tissue causing the chondrocytes to depend on nutrient diffusion rather than vascular supply of the material necessary for cell survival. Three types of cartilage exist in the human anatomy, hyaline cartilage, fibrocartilage, and elastic cartilage. The most common cartilage in orthopedic applications is hyaline cartilage forming the articular surfaces of bones and fibrocartilage forming the discs within the joint structure.

The open cells of the cancellous tissue 78 contain red marrow. Flat and irregular bones such as vertebrae are constructed like the epiphyses of long bones. An external layer of thin cortical bone, or articulating cartilage at the portion of the bone forming a joint, encapsulates the cancellous bone tissue. The resulting structure is similar to foam injection molded parts used in the construction of electronic equipment, where a solid outer shell of plastic supported by an inner core of foam provides a lightweight construct suitable for resisting the mechanical stresses applied to the device. As with the cancellous tissue of the epiphysis of long bones, the space within the cancellous bone fiber matrix in flat and irregular bones is occupied by red marrow.

There are a number of injuries or surgical procedures that require defects in bone or cartilage to be repaired. In some instances, bone is removed from one portion of the body, the harvest site, and transferred to another portion of the body to repair a wound or otherwise treat a patient (e.g. cartilage repair, spinal fusion). Depending upon the procedure being performed, the implant of the subject invention may be suitable for the original tissue defect and also beneficial for treating the harvest site. One such surgical procedure that creates a harvest site is the Arthrex (Naples, Fla.) Osteochondral Autograft Transfer System (OATS) for treating full thickness femoral condylar defeats in the knee. This procedure uses a series of thin-walled cutting tubes to harvest autogeneous plugs of bone capped with healthy hyaline cartilage which will be transferred to the damaged area. These osteochondral core autografts are then press fit into one or more sockets created in the condylar defect.

The OATS technique may be carried out arthroscopically or as an open procedure based on surgeon preference and the location and extent of the chrondral defect and harvest site. The preferred donor site is lateral on the lateral femoral chondyle just above the sulcus terminalis. This area has a convex curvature on its articular surface similar to that of the central weight-bearing areas of both femoral chondyles.

Donor sockets are routinely left open after these types of tissue harvesting procedures.

Figure 6:
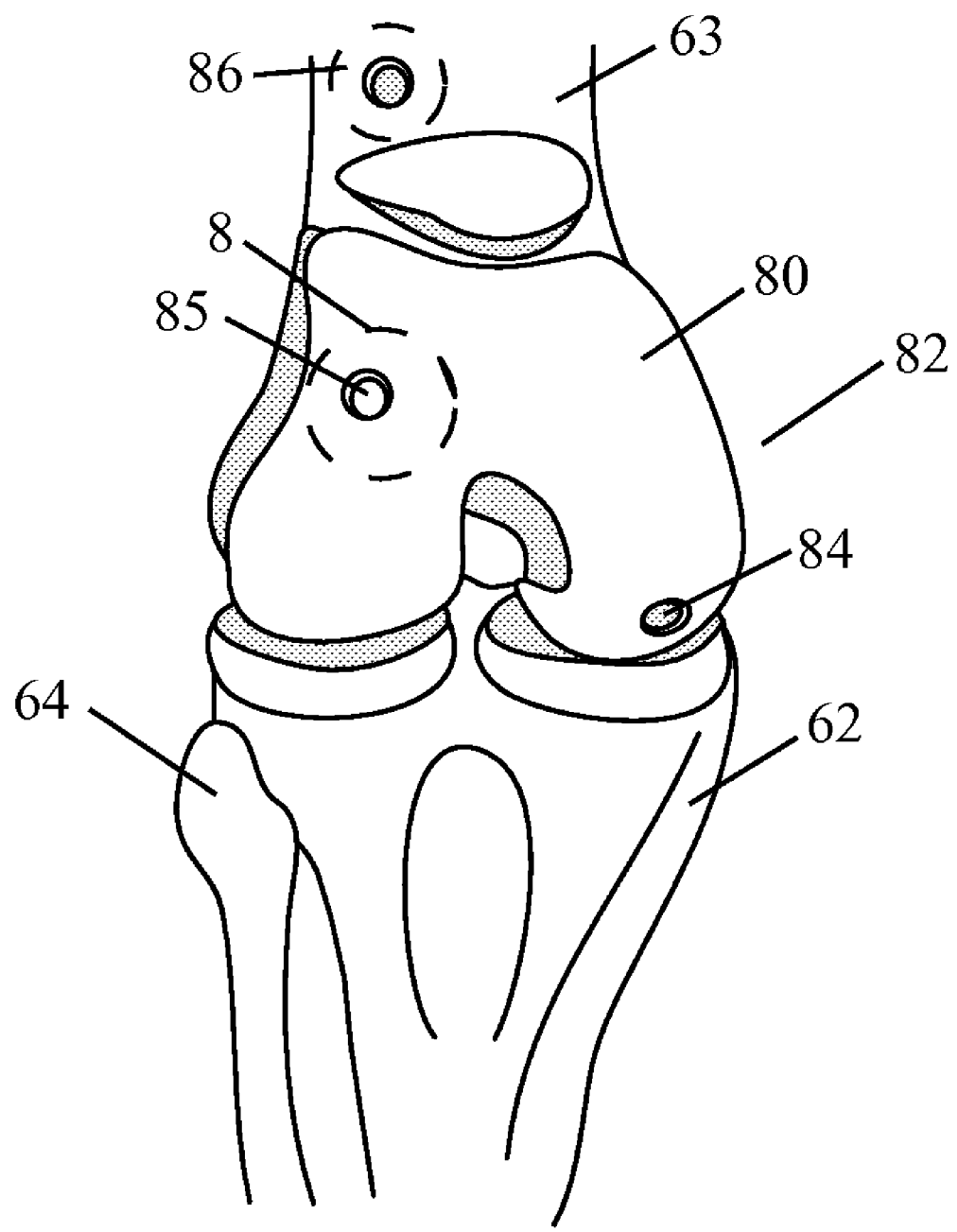
FIG. 6 is an enlarged detailed perspective view of a portion of the tissue shown in FIG. 4.

FIG. 6 depicts a close-up illustration of the femur tibia joint 82 shown in FIG. 4. Tissue defects 84, 85, and 86 are shown. Defects 84 and 85 extend through the articular cartilage layer 80 and into the cancellous bone. Tissue defect 86 is shown extending into the cancellous bone (see 78 of the femur 63, in FIG. 5).

Figure 7:
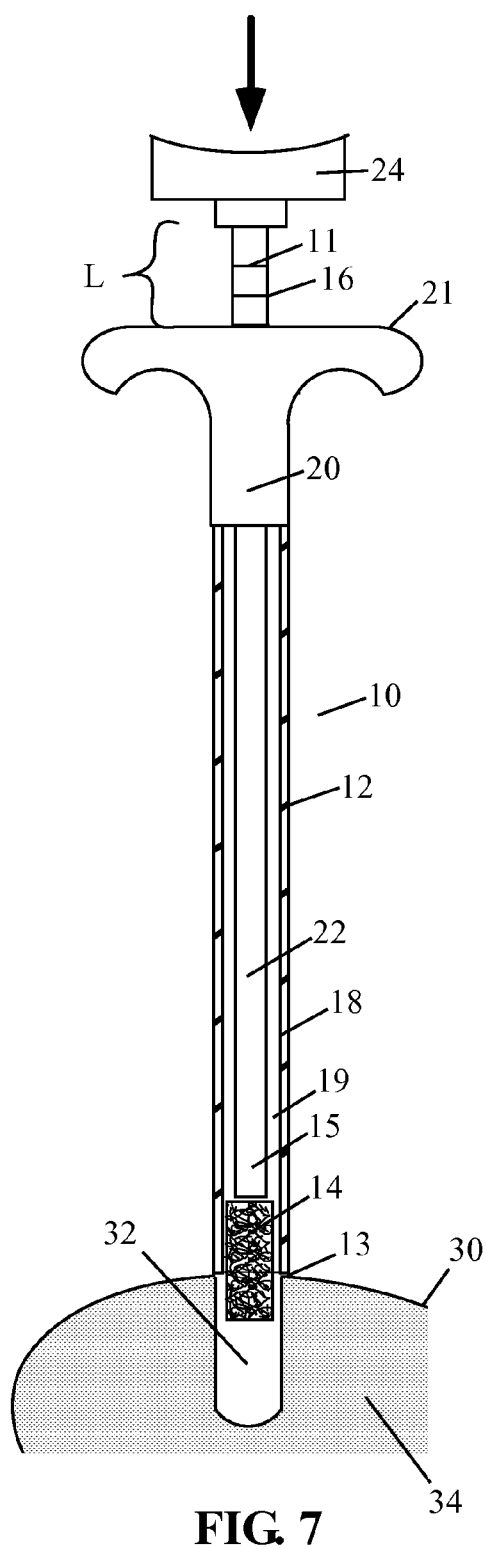
FIG. 7 illustrates in plan view a tissue treatment system of the present invention, partly cut away to show in cross-section its constituent components, delivering an implant into tissue of a living being.
Figure 8:
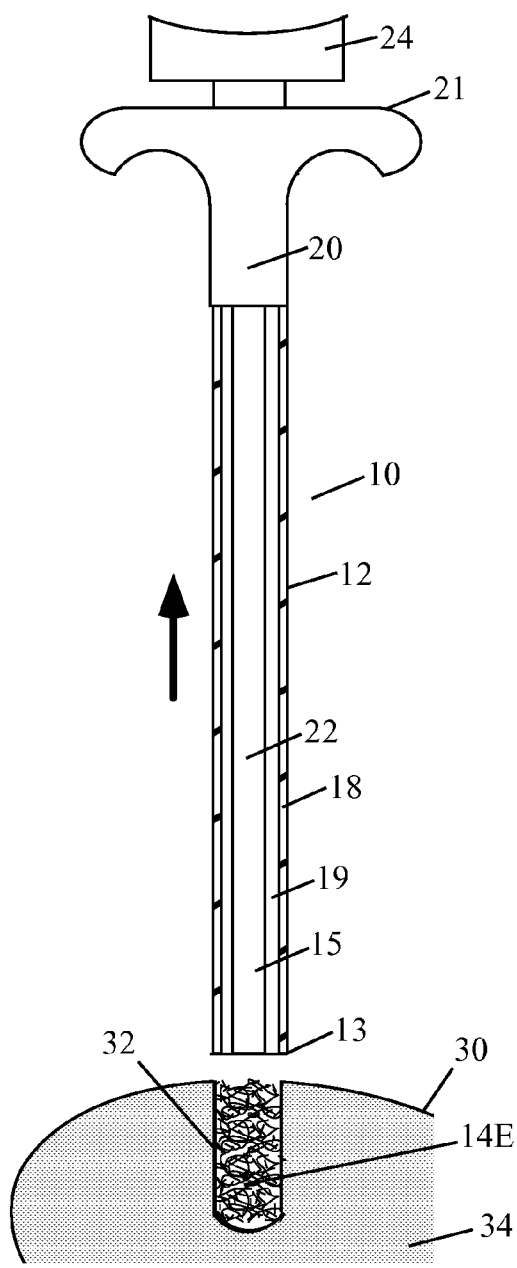
FIG. 8 illustrates in plan view a tissue treatment system of the present invention, partly cut away to show, in cross-section its constituent components, being removed from the tissue after delivering an implant into the tissue of a living being.

The application of the implant of the subject invention to the tissue defect will now be described. According to the procedure of the present invention and as shown in FIG. 7, the surgeon positions the distal end of sheath 13 at the defect site 32 of the tissue 30. As shown in FIG. 7 the sheath tip 13 can be sized to abut the outside of the wound site or the sheath tip could be sized to fit within a portion of the wound (not shown). Once the treatment system 10 is properly positioned, the surgeon applies pressure to thumb plate 24 of applicator 16. As plunger 22 slides through sheath 12 it advances the implant material 14 until the material exits the sheath. Note, the length "L" of the proximal end of the plunger extending from the proximal end of sheath 12 may be calibrated to exact length of the implant device 14, so that the surgeon can accurately determine when device 14 is just fully within the distal end of sheath 12. The indicator markings 11 allow the surgeon to gauge how far the implant is advanced into the tissue defect. As shown in FIG. 8, when thumb plate 24 of applicator 16 abuts hub 20, the physician knows that implant 14 has been pushed entirely out of lumen 19 and that the distal end of plunger 22 is substantially flush with the distal end of sheath 12. The surgeon can alternatively directly visualize the placement of the implant when a transparent or translucent material is used for sheath 12. As the advancing implant 14 engages the tissue defect site, the physician will encounter resistance at thumb plate 24. He/she then may maintain axial pressure so as to hold the implant 14 against the defect site. In the instance where the defect site is bleeding, the implant 14 may be mechanically held against the site of bleeding to achieve immediate hemostasis. As the implant material (e.g. collagen) begins to interact with bleeding tissue, self-sustaining hemostasis begins to take over, and shortly thereafter mechanical pressure will no longer be needed. As shown in FIG. 8, once the implant 14 is suitably positioned system 10 can be removed from the defect site. As described previously the implant 14E may expand to fill the defect site.

Figure 9:
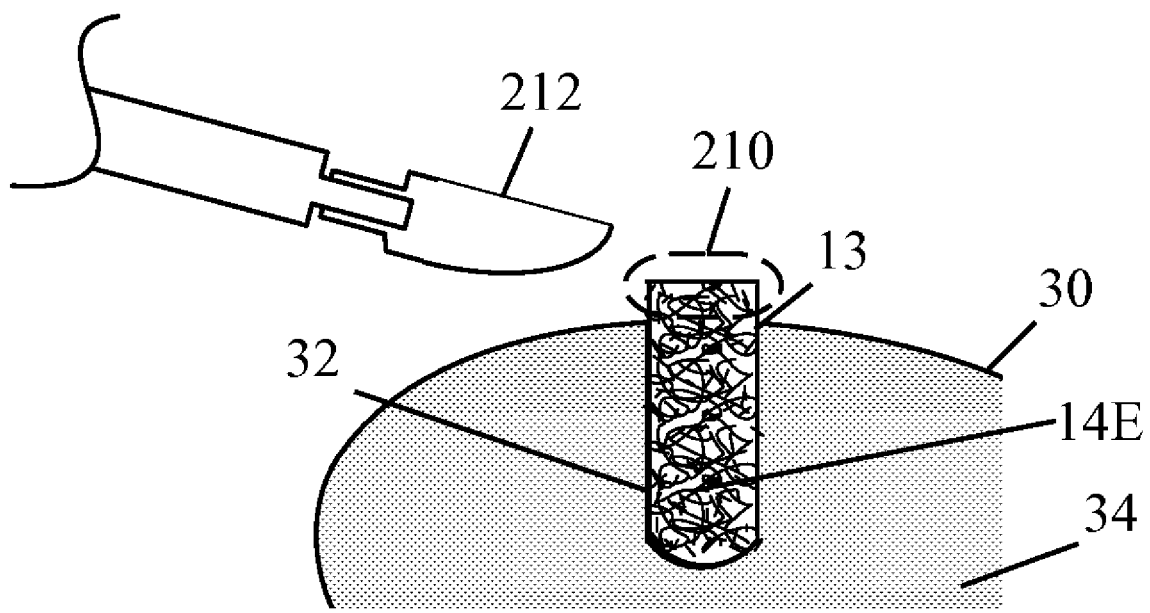
FIG. 9 illustrates a cross-sectional view of the treated tissue, containing an implant, and an instrument for contouring the implant.

In some situations, the length of the implant 14 may need adjustment. If the implant material is too short and does not properly fill the defect site then multiple implants may be inserted. As shown in FIG. 9, if the implant is too long (e.g. a portion of the implant extends from the wound), the undesired portion of the implant 210 can be removed with a suitable trimming tool 212 (e.g. scalpel, scissors). It is also conceivable that the delivery system 10 may incorporate a cutting blade, knife or other tool at its distal end (not shown) for purposes of reshaping the implant.

In some instances, the defect site may need to be modified to remove non-viable tissue or otherwise adjust the size of the defect. FIG. 10 depicts a coring tool 110 that can be used both to remove a healthy harvest tissue plug for use at a defect site and to reshape a defect site to allow for a better fit of a tissue implant. The coring tool 110 has a generally cylindrical distal portion 140 and distal tip 130 both of which are formed of a hardened stainless steel. The distal portion 140 may have indicator markings 132 to help gauge the depth of the tool with respect to the wound site during the coring process. The main body of the coring tool 138 has a proximal segment and may have a knurled portion 136 to provide the surgeon with a good gripping surface, and a proximal surface 134. The coring tool also includes a coring sleeve 142 consisting of an elongated thin walled tube 143 with a cylindrical knob 144 on the proximal end. The coring tool 110 and coring sleeve 142 are assembled as shown in FIG. 11 and hammered or otherwise inserted into the wound site. With this tool, an irregular wound site 146 can be shaped into a more regular modified wound site 148 by removing portions of the bone 150 from the wound site.

It is anticipated that the coring tool 110 may be available in a number of sizes to address the variety of tissue defect configurations that may be encountered. The tissue defect can be inspected either arthroscopically or directly and the size thereof can be measured. The appropriate coring tool/delivery system 110 can be selected (e.g., 5, 6, 7, 8, 9, 10 mm diameters on the distal core tool tip 140). These coring tools can be color-coded to correspond in size with the diameter of the defect and with the implant sizes and delivery system. Using a sturdy mallet, the coring tool 110 is then driven into the bone 152 to the desired depth (e.g. 15 mm) and the core material 150 can be removed. As depicted in FIG. 9, when used properly the tool can be used to change an irregularly shaped defect site 146 into a more regularly sized implant site 148.

The core tool inner sleeve 142 can be removed from the core tool body 138 to provide a clear delivery path for the implant material into the modified wound site 148. The removed tissue or bone 150 is autologous material and may contain active growth factors or other beneficial components and as such may be further modified (e.g. ground-up) and used for insertion into this or other wounds, or incorporated into the implant 14, to help stimulate healing.

The coring tool can also be used as a delivery instrument as shown in FIG. 13. In this alternative embodiment, the implant material can be loaded into the delivery system while the delivery system (e.g., coring tool 110) is pre-positioned at or within the defect site. Thus, as shown in FIG. 11, after the coring tool 110 has been inserted so that its outlet 130 (as shown in FIG. 10) is within the wound a pusher 154 can be extended or pushed down the central passageway 156 as described heretofore so that its distal end portion 155 forces the implant 14 towards outlet 130. After the implant is pushed to the end of the central passageway 156 by the pusher 154, the tubular body 138 is itself withdrawn from the wound 148 and moved completely outside the body of the patient. This action leaves the implant 14 within the wound.

Figure 14:
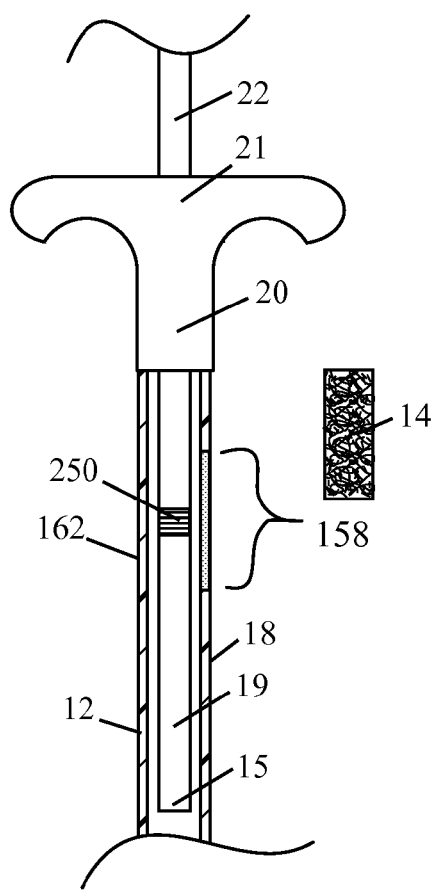
FIG. 14 is a side view in partial cross-section of a portion of one embodiment of the treatment system of the subject invention shown prior to loading of the implant material into the system.
Figure 15:
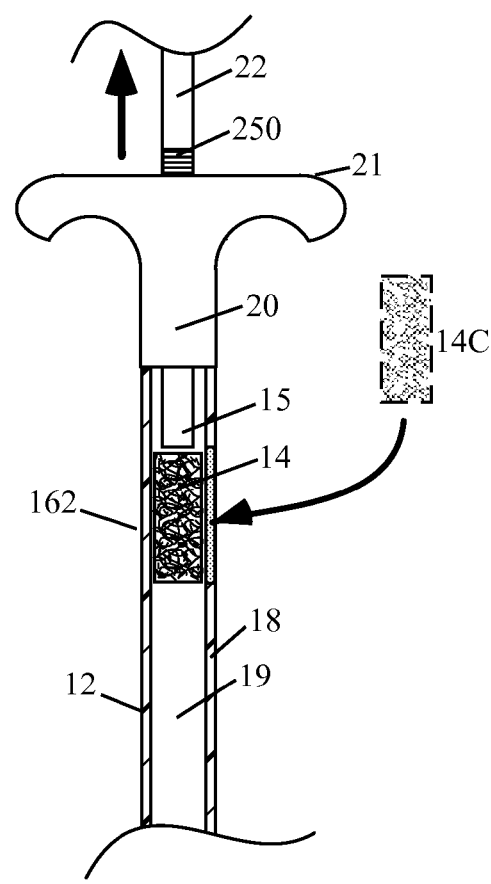
FIG. 15 is a side view in partial cross-section of a portion of one embodiment of the treatment system of the subject invention shown with an implant loaded within the system.
Figure 16:
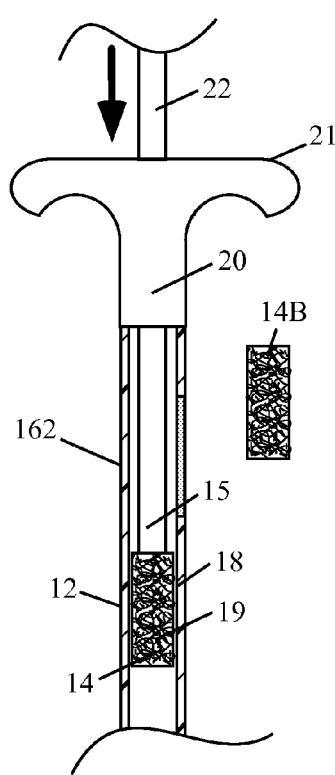
FIG. 16 is a side view in partial cross-section of a portion of one embodiment of the treatment system of the subject invention shown with an implant loaded and being advanced within the treatment system.

It should also be readily apparent from the above description that more than one implant device 14 could be used. For the tissue defect treatment systems 10 and 110 and, if the physician were to decide to use more than one plug, he/she need only remove plunger 22, insert a implant 14 (of the same or different material) into the proximal end of lumen 19 and then reinsert plunger 22 behind it. Alternatively, the entire system 10 could be removed and replaced with a second one, which has been preloaded and is ready for immediate use. Thus, it will be appreciated that a second, third, etc., implant 14 may be delivered and applied to the defect site or to multiple defect sites during a procedure. FIGS. 14-16 describe another method for loading multiple implants 14 into the body of a patient through an alternate delivery treatment system 162. FIG. 14 shows tissue defect treatment system 162 generally comprises a sheath 12, and a mass of implant material 14.

It is further contemplated that multiple implants of various compositions may be delivered to the same site, or other nearby sites. The various compositions may be selected for any number of reasons, including but not limited to, the delivery of various therapies or various degrees or types of bio-matching (e.g., porous center or deep region followed with a hard surface component/implant).

Sheath 12 generally comprises a tubular housing 18 defining a lumen 19, a hub 20 disposed at the proximal end of housing 18. In general, the tubular housing 18 has a window 158 formed in a portion of the wall of the tube for purpose of inserting implant devices 14. The size of the window is chosen so as to permit entrance of a variety of sizes of the implant 14. The system uses an applicator (not shown in entirety) similar to applicator 16 in FIG. 1. The applicator basically comprises an elongated, cylindrical rod-like plunger 22 having a thumb plate (not shown) disposed at its proximal end and a distal end 15. To load implant 14 into the device, plunger 22 is retracted until the distal portion 15 is proximal to the window 158 in tubular housing 18 and indicator marks 250 on plunger 22 are visible as shown in FIG. 15. Plunger 22 is then advanced and implant 14 is transferred through the sheath 18 to the target site. Another plug 14B could be loaded and positioned into window 158, as shown in FIG. 14, and then directed toward the same or another tissue defect site. This system may have particular advantages during an endoscopic procedure where the physician does not want to remove the delivery system from the patient to deliver additional plugs, such plugs may be of different composition 14C. With system 162 the sheath 12 remains within the patient and additional implants can be loaded into the device.

Figure 17:
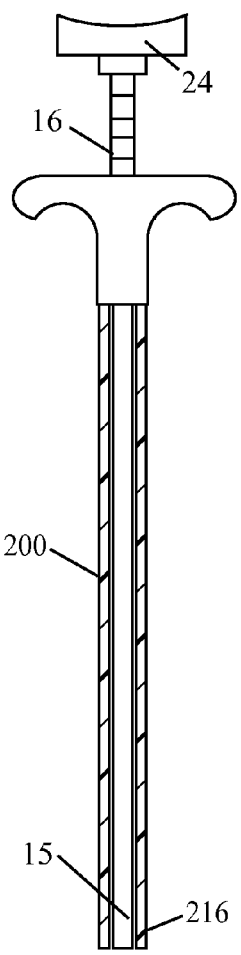
FIG. 17 is a plan view of yet another embodiment of the tissue treatment system 200 of the present invention, partly cut away to show in cross-section its constituent components, including a sheath, an applicator plunger.
Figure 18:
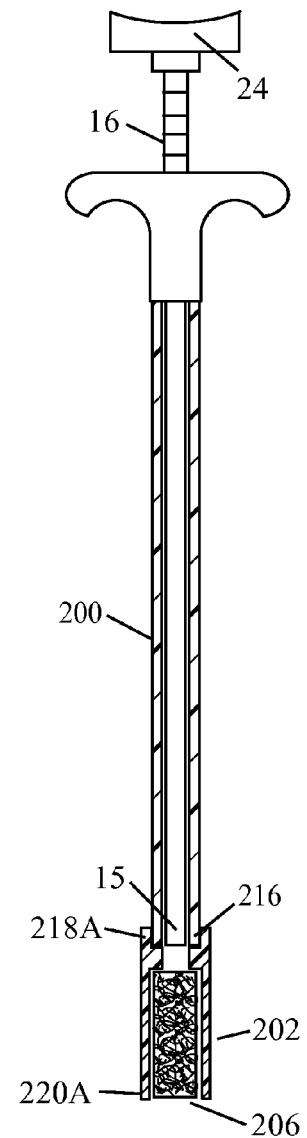
FIG. 18 is a plan view of the tissue treatment system 200 shown in FIG. 17 assembled to an implant carrying device 202.
Figures 19, 20, 21:
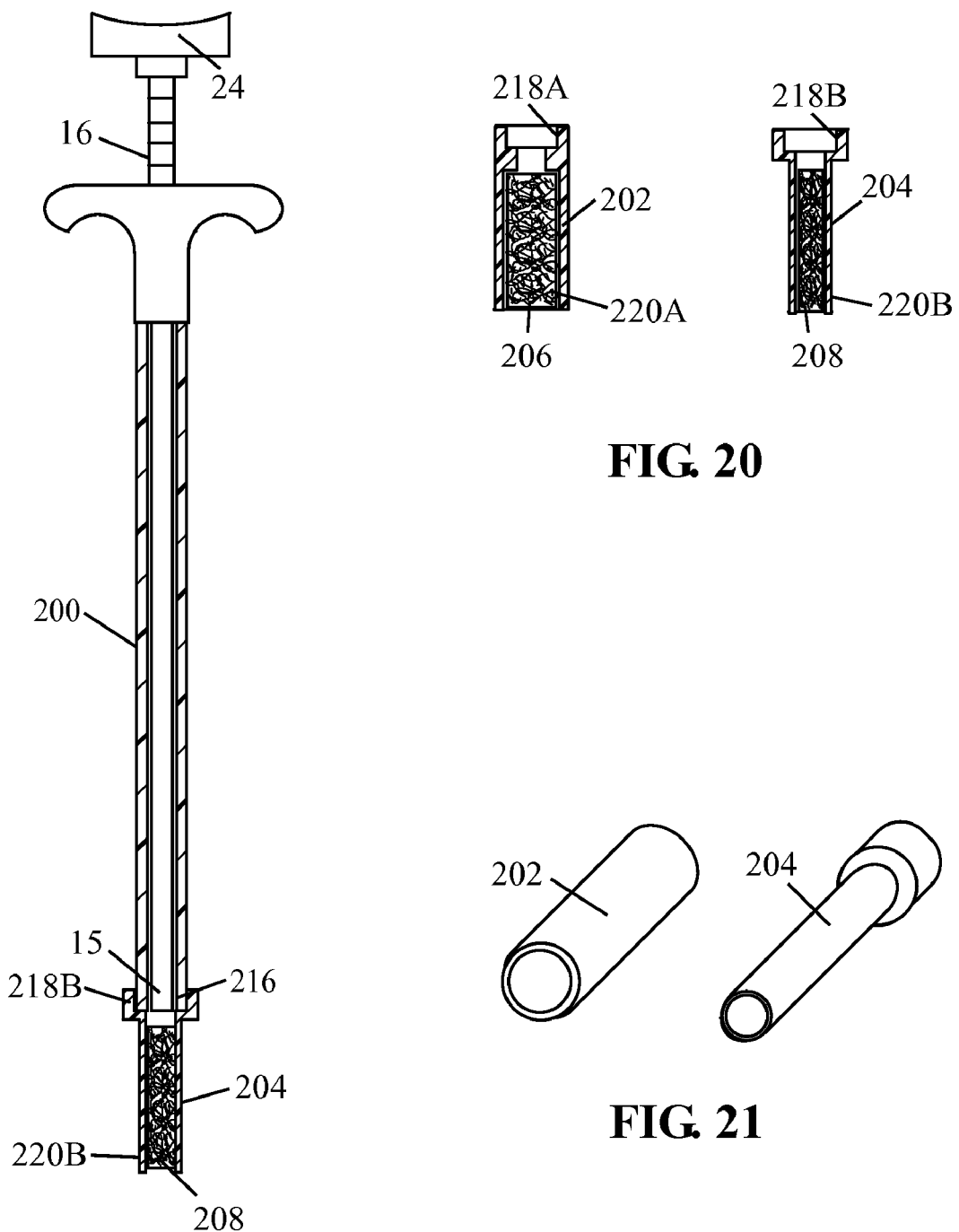
FIG. 19 is a plan view of the tissue treatment system 200 shown in FIG. 17 assembled to another embodiment of an implant carrying device 204.
FIG. 20 is a side sectional view of the implant carrying devices shown in FIG. 18 and FIG. 19.
FIG. 21 is a perspective view of the implant carrying devices shown in FIGS. 18-20.

It is also conceivable that a cartridge or magazine of implants, similar to is used for delivering surgical staples, could be attached to the delivery system to provide automated or semi-automated loading of one or more implants. The cartridge could be designed to interface with window 158 or cartridges could be designed to connect directly to the distal portion of applicator 16 as shown in FIG. 17-19. Treatment system 200, shown in FIG. 17 is similar to treatment system 10 of FIG. 1 except that it can be used in conjunction with the implant carrying cartridges 202 and 204 shown in FIGS. 18-21. The cartridges are essentially thin walled cylindrical tubular structures designed to store implant devices. The cartridges can be fabricated from thin walled stainless steel or injection molded polymers such as polycarbonate. The cartridges 202 and 204 can be sized to hold implants of various outer diameters and lengths. By way of example, cartridge 202 can accommodate large diameter implant 206 and cartridge 204 can accommodate small diameter implant 208. The cartridges are designed to attach to the distal portion 216 of treatment system 200. The proximal segment of cartridges 202 and 204 has an attachment portion 218A and 218B that connects to the distal portion 216 of the treatment system. The attachment can be by way of a tapered interference fit, screw thread, bayonet attachment, dimpled attachment ring or any other [means] know to those skilled in the art. The size and length of the desired implant and related cartridge can be selected by the surgeon and attached to the treatment system. The distal portion of the cartridge 220A and 220B is positioned at the desired site and the thumbplate 24 can be depressed to advance the distal end 15 of the applicator 16 into contact with the implants 206 and 208 to eject the implants from the cartridge sleeves 202 and 204. Once the implant is ejected, the empty cartridge sleeve 202 or 204 can be removed and replaced with another cartridge.

The design of treatment system 200 allows one delivery system to be used to delivery one or more similar or different sized implants.

Additionally, these embodiments may be used to deliver a plurality of flowable implants, wherein indicator markings 250 may be used to measure the amount of each implant. Likewise, the coring tool 110 may be used to remove material to a certain depth, or a measured depth, as indicated by core depth indications 154. The amount of implant material 14 necessary to fill the voids or defects may be calculated or determined by correlating coring indication markings 145 with plunger markings 250. This correlation may be performed whether the coring tool 110 is used separately from the system 10, or whether the plunger mechanism 22 is fed through the core tool body 138 (i.e., whether two instruments are used, or both steps are performed through the single tool, as previously discussed) as previously described.

Figure 22:
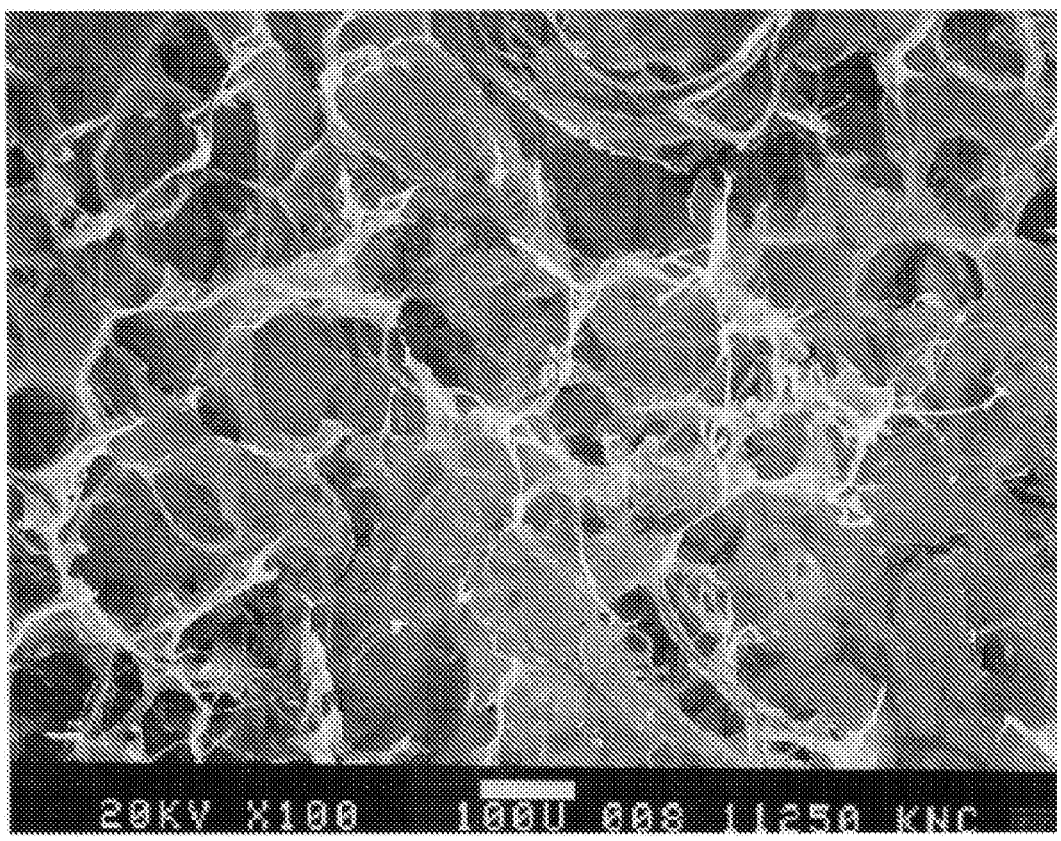
FIG. 22 depicts a 100× Scanning Electron Microscope image of a bone replacement material. This implant is composed of Kensey Nash P1076, a bovine hide-derived collagen material that is a combination of native collagen fibers and soluble collagen. The pores comprising the macrostructure of the implant are between 100-um and 200-um in diameter.

FIG. 22 depicts a 100× Scanning Electron Microscope image of an embodiment of a bone replacement material. This implant is composed of Kensey Nash P1076, a bovine hide-derived collagen material that is a combination of native collagen fibers and soluble collagen. The pores comprising the macrostructure of the implant are between 100-um and 200-um in diameter.

Figure 23:
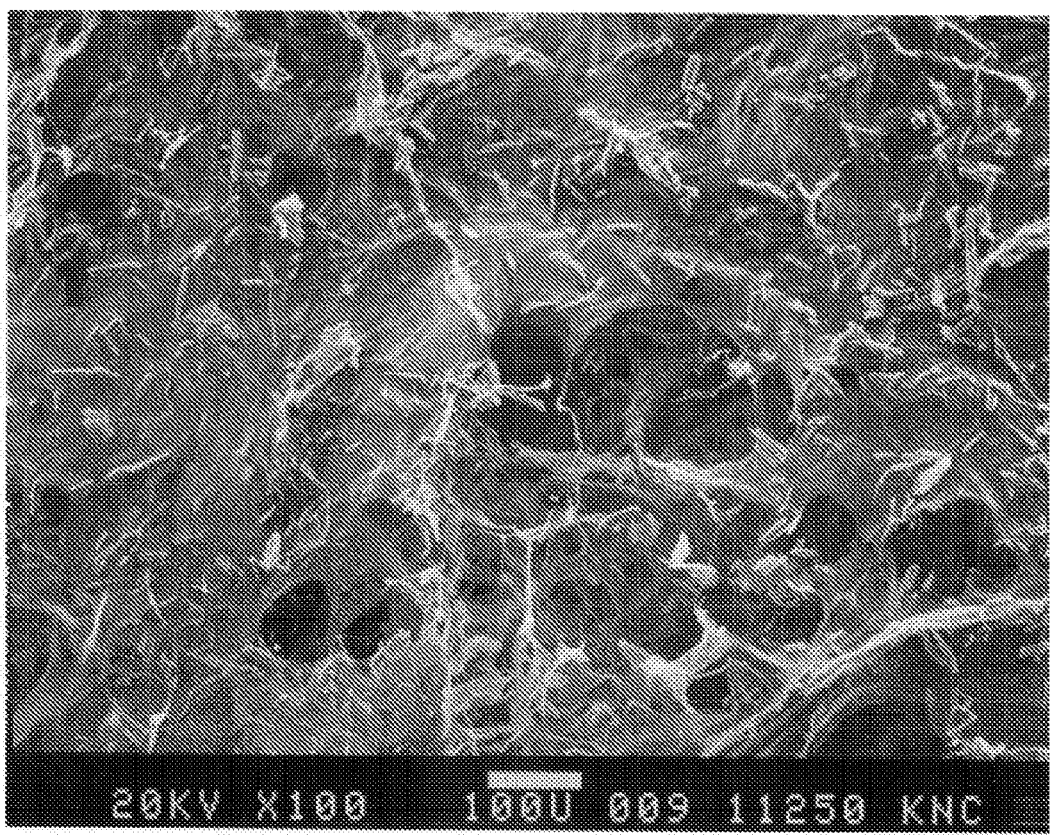
FIG. 23 depicts a 100× Scanning Electron Microscope image of a bone replacement material. A constituent of this implant is Kensey Nash P1076, a bovine hide-derived collagen material that is a combination of native collagen fibers and soluble collagen. Blended into the collagen at 25% by weight is medical grade calcium sulfate, shown as the small cylindrical particles throughout the porous macrostructure.

FIG. 23 depicts a 100× Scanning Electron Microscope image of a bone replacement material. A constituent of this implant is Kensey Nash P1076, a bovine hide-derived collagen material that is a combination of native collagen fibers and soluble collagen. Blended into the collagen at 25% by weight is medical grade calcium sulfate, shown as the small cylindrical particles throughout the porous macrostructure.

Figure 24:
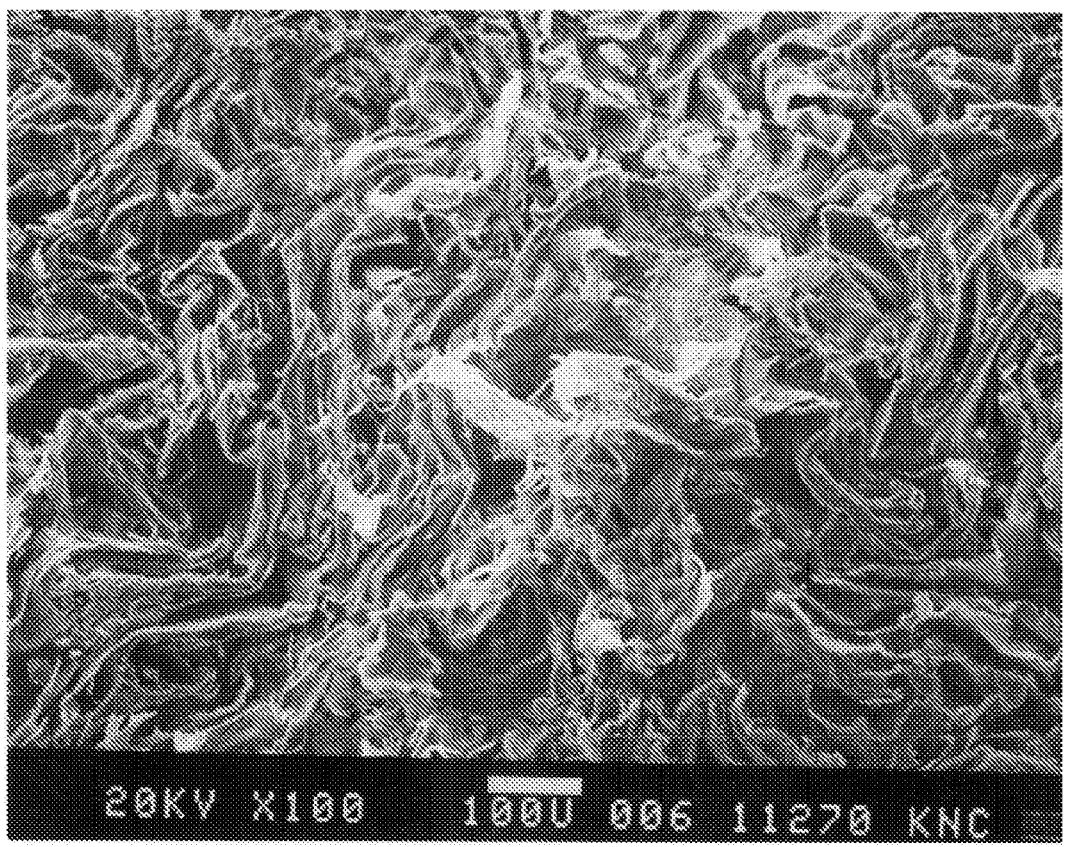
FIG. 24 depicts a 100× Scanning Electron Microscope image of a bone replacement material. This implant is composed of Kensey Nash P1076, a bovine hide-derived collagen material that is a combination of native collagen fibers and soluble collagen. This implant has been crushed by approximately 233% causing the pore size to decrease to 20-um to 50-um.

FIG. 24 depicts a 100× Scanning Electron Microscope image of an embodiment of a bone replacement material. This implant is composed of Kensey Nash P1076, a bovine hide-derived collagen material that is a combination of native collagen fibers and soluble collagen. This implant has been crushed by approximately 233% causing the pore size to decrease to 20-um to 50-um, thereby imparting a bio-matched condition, more specifically, a porosity matched or compliance matched condition.

Figure 25:
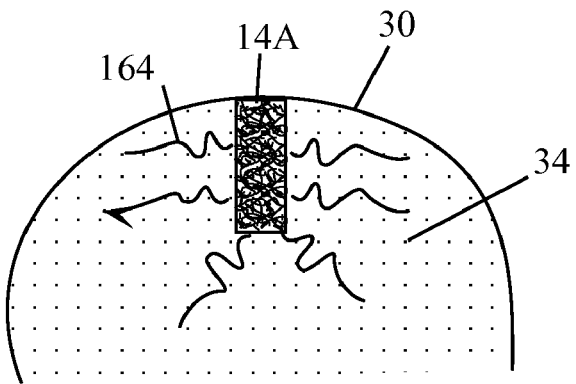
FIG. 25 is a cross-sectional view of tissue containing an embodiment of the implant of the subject invention that releases and agent to treats the local tissue.

As described previously, the implant can be used to deliver a variety of agents (e.g., drugs, biologics, etc.) into the patient's body. FIG. 25 depicts agent elution 164 from implant 14A. In this embodiment, the implant may be constructed to effect an immediate or time-phased delivery of one or more active ingredients. The presence of the implant and delivery of selected agents is designed lead to improvements in patients with tissue defects through at least one of several methods such as: (1) an agent or biologic can act as a signaling molecule to activate a proliferating or differentiating pathway, (2) an agent may act as a depot for nutrients for proliferating and growing cells, and (3) an agent may prevent an adverse tissue response to the implant.

In the preferred embodiment shown in FIG. 25, agent delivering implant material 14A, the device provides continuous smooth release of the active agent 164 over all or some of the degradation period of the device. In another preferred embodiment, the agent is released at all times during which the device remains in the tissue. In certain applications it may be necessary to provide one or more burst releases of the active agent. The device may also be designed to deliver more than one agent at differing or staged intervals and dosages. It is also conceivable that the implant 14A may be designed to hold the agent within the boundary of the device (e.g. not release the agent to surrounding tissues) so as to affect only those cells that migrate into the porous structure of the device.

As a non-limiting example, implant 14A could incorporate microparticles within its structural framework. The particles degrade after implantation in the body of a living being and can be used to deliver any type of molecular compound, such as proteins, genetic materials, peptides, pharmacological materials, vitamins, sedatives, steroids, hypnotics, antibiotics, chemotherapeutic agents, prostaglandins, and radiopharmaceuticals. The delivery system of the present invention is suitable for delivery of the above materials and others, including but not limited to proteins, peptides, nucleotides, carbohydrates, simple sugars, steroids, pharmaceuticals, cells, genes, anti-thrombotics, anti-metabolics, growth factor inhibitor, growth promoters, anticoagulants, antimitotics, and antibiotics, fibrinolytic, anti-inflammatory steroids, and monoclonal antibodies. Microspheres can be made of a variety of materials such as polymers, silicone and metals. Biodegradable polymers are ideal for use in creating microspheres. Several variables can influence the mechanism and kinetics of polymer degradation, for example, material properties like crystallinity, molecular weight, additives, polymer surface morphology, and environmental conditions. As such, to the extent that each of these characteristics can be adjusted or modified, the performance of this invention can be altered.

Figure 26:
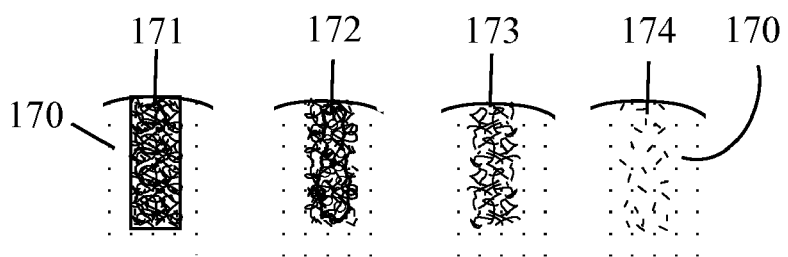
FIG. 26 is a cross-sectional view of a tissue containing an embodiment of the implant of the subject invention showing the gradual resorption of the implant and tissue regeneration occurring over time.

After the implants of this invention are positioned within the structure of the body of the living being, the portions of the device will degrade or resorb as new cells and tissue migrate into the implant. FIG. 26 depicts the tissue defect site and implant over time. Implant 171 is shown at an early time point right after implantation, implant 172 is shown at some later time point, implant 173 at yet a later time point, and implant 174 is shown at a fourth time point at which the implant is nearly completely resorbed and replaced by healthy tissue 170.

Figure 27:
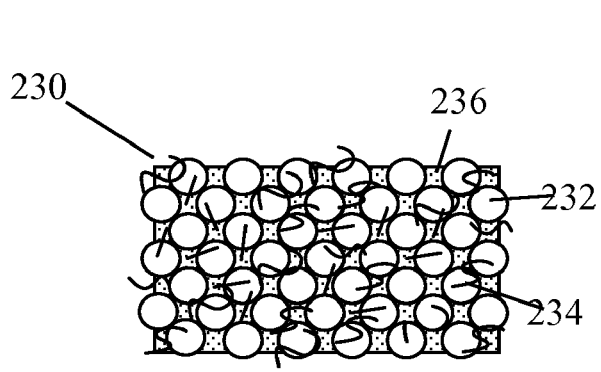
FIG. 27 is a cross-sectional close-up view of one embodiment of the implant material of the subject invention.

FIG. 27 depicts a magnified view of a portion of yet another embodiment of the implant device 230 that is comprised of a series of spherical like structures or beads 232 that are connected together to form a macrostructure or framework for the implant device 230. The beads 232 can be made from a variety of materials such as calcium alginate, polylactic acid, gelatin or any other suitable biomaterial described herein or known to those skilled in the art. This particular embodiment may also incorporate native collagen fibers 234 and a filling material 236. The filling material can be a made from a more soluble collagen such as Semed S manufactured by Kensey Nash Corporation of Exton, Pa. or another biomaterial known to those skilled in the art.

Figure 28:
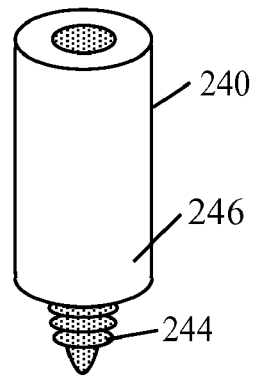
FIG. 28. is a perspective view of an alternative embodiment of the implant 240 of the subject invention.

FIG. 28 depicts yet another embodiment of the implant material, implant 240, that includes an anchoring element 244. The anchoring element can be used to hold implant 240 in the defect site during the healing of the defect.

Figure 29:
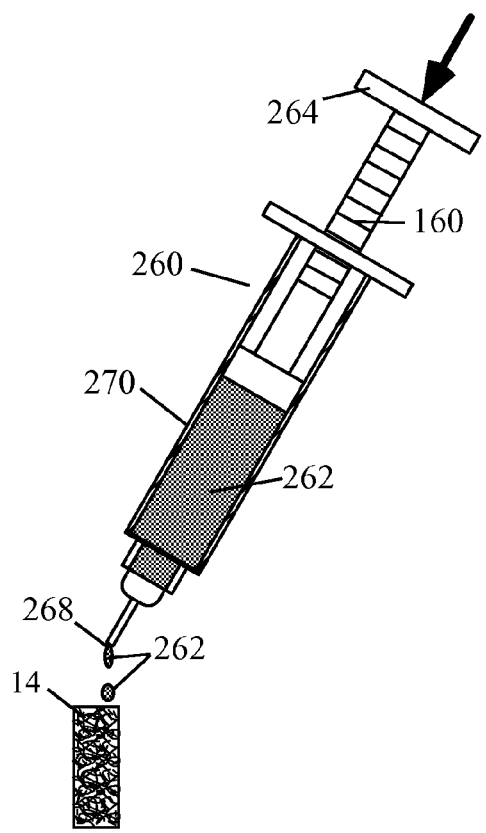
FIG. 29 is a side view in partial cross-section of an embodiment of an agent delivery system loading an implant with an agent.

FIG. 29 depicts an embodiment of an agent delivery system (e.g. syringe) that is actively loading implant 14 with an agent (e.g. bone marrow cells, growth factors, antibiotics, etc.). In this embodiment, the agent 262 is drip-loaded into the implant 14 prior to placement within a delivery system and hence prior to implantation in the living being. The delivery system 260 comprises a syringe-like body 270, which contains the agent 262. The agent plunger 264 is advanced in the direction of the arrow to dispense the agent from the distal exit orifice 268 of the system 260. A preset quantity of agent can be applied to the implant or surrounding tissue depending upon the application. Markings (not shown) can be used to measure the amount of agent applied. It is also conceived that the implant could be loaded with an agent while stored within a delivery system and also loaded with the agent after the implant is positioned into the tissue of the living being.

Figure 30:
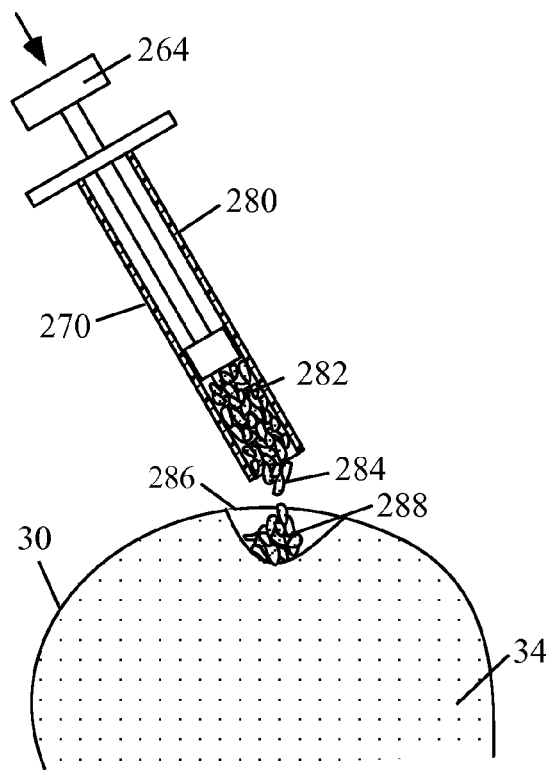
FIG. 30 is a side view in partial cross-section of a portion of a delivery system applying yet another embodiment of an implant of the subject invention.

FIG. 30 is a side view in partial cross-section of a portion of a delivery system applying yet another embodiment of an implant of the subject invention. This segmented implant delivery system 280 is suitable for delivery of implants 282 that are comprised of multiple segments (e.g. granules, chips, fibers, etc.). These implants may be more suitable for filling non-uniform or irregular tissue defects 286 in tissue of a living being 30. The syringe-like delivery system utilizes a cylindrical housing body 270 to hold the material and a plunger 264 to eject the material from the distal opening of the syringe body. The segmented implant can flow or be otherwise distributed to fill the void. The implant material can be of any material or combination of materials previously described herein.

Numerous other embodiments and modifications will be apparent to those skilled in the art and it will be appreciated that the above description of a preferred embodiment is illustrative only. It is not intended to limit the scope of the present invention, which is defined by the following claims. Without further elaboration the foregoing will so fully illustrate our invention that others may, by applying current or future knowledge, adopt the same for use under various conditions of service.

What is claimed is:

1. A flowable implant for the repair or regeneration of an internal tissue in a living being, said implant comprising a tissue conductive matrix and at least one calcium salt blended into said matrix, at least a portion of said matrix comprising a blend of soluble collagen and native insoluble collagen fibers and where at least a portion of said collagen is prepared from porcine tissue, wherein at least a portion of said implant is porous, and further wherein said porous implant has a pore size that is at least about 100 microns, and still further wherein said porous implant is arranged to be implanted in the body of said living being, said matrix being compressed prior to the implant procedure, wherein elastic recovery from said compression occurs following release into defect site and causes said implant to conform to the shape of the defect being treated.

2. The implant of claim 1, wherein said portion of said collagen derived from porcine tissue comprises native collagen fibers.

3. The implant of claim 2, wherein said porcine tissue derived collagen comprises biological constituents.

4. The implant of claim 3, wherein said biological constituents comprises at least one of angiogenic agents, anti-inflammatory agents, arteriogenesis agents, chondroitin, cytokines, prostaglandins, glycosaminoglycans, growth factors, heparin, hyaluronic acid, integrins, peptides, polypeptides, proteins, proteoglycans, or combinations thereof.

5. The implant of claim 2, wherein porcine tissue derived collagen comprises cellular materials.

6. The implant of claim 5, wherein said cellular materials comprise at least one of glycoproteins, growth factors, and sources of growth factors.

7. The implant of claim 2, wherein the native collagen fibers further comprise at least one of elastin, hyaluronic acid, polysaccharides, salts.

8. The implant of claim 1, wherein said matrix further comprises a therapy comprising at least one drug or biologically active agent.

9. The implant of claim 1, wherein said matrix further comprises at least one additional polymer.

10. The implant of claim 9, wherein said additional polymer is synthetic.

11. The implant of claim 9, wherein said additional polymer is at least partially bio-resorbable.

12. The implant of claim 11, wherein said additional polymer comprises chitin, PGA/PLLA copolymers, hydrogel, Lactide/.mu.-caprolactone copolymers, PGA, PLA, or PCL.

13. The implant of claim 9, wherein said additional polymer is osteoinductive.

14. The implant of claim 1, wherein said tissue conductive matrix further comprises at least one ceramic.

15. The implant of claim 14, wherein said ceramic comprises calcium phosphate, calcium sulfate, or hydroxyapatite.

16. The implant of claim 14, wherein said at least one ceramic is in the form of particles blended with said tissue conductive matrix.

17. The implant of claim 1, wherein said matrix further comprises reconstituted collagen.

18. The implant of claim 1, wherein said tissue conductive matrix is bio-matched.

19. The implant of claim 18, wherein said bio-matched, tissue conductive matrix comprise a matrix that is at least one of integrity matched, porosity matched, compliance matched or weight matched.

20. The implant of claim 1, wherein said pores make up more than 50 percent by volume of said porous portion.

21. The implant of claim 1, wherein said implant is located in said living being at a site of a bone defect.

22. A flowable implant for the repair or regeneration of an internal tissue of a living being, said implant comprising a tissue conductive matrix and at least one calcium salt blended into said matrix, at least a portion of said matrix comprising a blend of soluble collagen and native insoluble collagen fibers, and where at least a portion of the collagen is prepared from porcine tissue, wherein at least a portion of said implant is porous, and further wherein said porous implant has a pore size that is at least about 100 microns, and further wherein said implant being in a form selected from the group consisting of a sponge and a loose, fibrous material, and still further wherein said implant is arranged to be implanted in the body of said living being, said matrix being compressed prior to the implant procedure, wherein elastic recovery from said compression occurs following release into defect site and causes said implant to conform to the shape of the defect being treated.

23. The implant of claim 22, wherein said portion of said collagen derived from porcine tissue comprises native collagen fibers.

24. The implant of claim 23, wherein said porcine tissue derived collagen comprises biological constituents.

* * * * *